US005858994A

United States Patent [19]
Kretzschmar et al.

[11] Patent Number: 5,858,994
[45] Date of Patent: Jan. 12, 1999

[54] CARBOHYDRATE CONJUGATES AS INHIBITORS OF CELL ADHESION

[75] Inventors: Gerhard Kretzschmar, Eschborn; Wolfgang Schmidt, Frankfurt; Ulrich Sprengard, Mainz; Eckart Bartnik, Wiesbaden; Dirk Seiffge, Mainz-Kostheim; Horst Kunz, Mainz, all of Germany

[73] Assignee: Hoechst Aktiengesellschaft, Germany

[21] Appl. No.: 509,079

[22] Filed: Jul. 31, 1995

[30] Foreign Application Priority Data

Oct. 10, 1994 [DE] Germany .......................... 44 36 164.5

[51] Int. Cl.$^6$ .............................. A01N 43/04; C07H 1/00; C07H 5/04; G01N 33/53
[52] U.S. Cl. .............................. 514/62; 514/54; 536/1.11; 536/55.1; 536/55.2; 536/123.1; 435/7.1
[58] Field of Search ........................... 514/54, 62, 123.1; 536/55.1, 55.2, 55.3, 1.11, 123; 435/7.1

[56] References Cited

U.S. PATENT DOCUMENTS 5,280,113  1/1994  Rademacher et al. .................. 536/55.2

FOREIGN PATENT DOCUMENTS

| 0 601 417 A2 | of 1993 | European Pat. Off. . |
| 601 417 A2 | 11/1993 | European Pat. Off. . |
| 0 606 925 | 7/1994 | European Pat. Off. . |
| WO 91/19501 | 12/1991 | WIPO . |
| WO 91/19502 | 12/1991 | WIPO . |
| WO 92/02527 | 2/1992 | WIPO . |
| WO 92/07572 | 5/1992 | WIPO . |
| WO 92/22565 | 12/1992 | WIPO . |
| WO 93/21948 | 4/1993 | WIPO . |
| 93/24506 | 12/1993 | WIPO . |
| 94/00477 | 1/1994 | WIPO . |

OTHER PUBLICATIONS

Hasegawa et al., "Synthetic Studies on Sailogylcoconjugates 52: Synthesis of Sialyl Lewis X Analogs Containing Aziodoalkyl Groups at the Reducing End", J. Carbohydrate Chemistry, 12(8), 1993, pp. 1203–1216.

Lee et al., "Binding Characteristics of Galactoside–binding Lectin (Galaptin) from Human Spleen", Journal of Biological Chemistry, vol. 265, No. 14, May 1990, pp. 7864–7871.

Ohbayashi et al., "Production of Monoclonal Antibodies Against Oligasaccharides Coupled to Protein", Carbohydrate Research, 236, 1992, pp. 349–356.

von dem Bruch et al., "Synthesis of N–Glycopeptide Clusters with Lewis Antigen Side Chains and Their Coupling to Carrier Proteins", Angewandte Chemie, 33, No. 1, 1994, pp. 101–102.

Stahl et al., "Synthesis of Deoxy Sialyl Lewis Analogues, Potential Selectin Antagonists", Angewandte Chemie, 33, No. 20, 1994, pp. 2096–2098.

Rio et al., "Synthesis of Glycopeptides from the Carbohydrate—Protein Linkage Region of Proteoglycans", Carbohydrate Research, 219, 1991, pp. 71–90.

Giannis, "The Sialyl Lewis$^x$ Group and its Analogues as Ligands for Selectins: 178–180 Chemoenzymatic Syntheses and Biological Functions" *Angew. Chem Int. Ed. Engl.,* 33(2): (1994).

Hughes, "Cell Adhesion Molecules—The Key To A Universal Panacea?", *Scrip Magazine,* 6:30–33 (1993).

Nifant'ev et al., "Neoglycoconjugates For Selectin Research: Design and Application," *Vortrag Glycotechnology Meetin La Jolla,* (1994).

Giannis, *Angew. Chem.,* 106: 188–191 (1994).

Mulligan et al., "Protective Effects of Oligosaccharides in P–Selectin–Dependent Lung Injury," *Nature,* 364: 149–151.

Wong et al., "Synthetic Glycosylation of Peptides Using Unprotected Saccharide β–Glycosylamines," *Glycoconjugate Journal,* 10: 227–234 (1993).

Buerke et al., "Sialyl Lewis$^x$ Containing Oligosaccharide Attenuates Myocardial Reperfusion Injury in Cats," *J. Clin. Invest.,* 93: 1140–1148 (1994).

Yoshida et al., "Synthesis of Chemically Modified Sialic Acid–Containing Sialyl–LK$^x$ Ganglioside Analogues Recognized by the Selectin Family," *Glycoconjugate Journal,* 10: 3–15 (1993).

Brandley et al., "Structure—Function Studies on Selectin Carbohydrate Ligands, Modifications to Fucose, Sialic Acid and Sulphate as a Sialic Acid Replacement," *Glycobiology,* 3: 633–639 (1993).

Nelson et al., "Higher–Affinity Oligosaccharide Ligands for E–Selectin," *J. Clin. Invest.,* 91: 1157–1166 (1993).

Toyokuni et al., "Synthetic Vaccines: Synthesis of a Dimeric Tn Antigen–Lipopeptide Conjugate That Elicits Immune Responses Against Tn–Expressing Clycoproteins," *J. Am. Chem. Soc.,* 119: 395–396 (1994).

*Primary Examiner*—John L. LeGuyader
*Assistant Examiner*—Mark L. Shibuya
*Attorney, Agent, or Firm*—Foley & Lardner

[57] ABSTRACT

The invention relates to novel conjugates of tetrasaccharides, preferably of sialyl-Lewis X (SLeX) and sialyl-Lewis A (SLeA), having improved activity as inhibitors of cell adhesion, a process for the preparation of these compounds, and their use as pharmacological active compounds and as diagnostics and pharmaceuticals which contain these conjugates.

34 Claims, 7 Drawing Sheets

(I-1) Y = NH(CO); n = 1; p = 1; R² = CH₂NH(CO)CH₂NH₂

| Y | n | p | R² | (I) |
|---|---|---|---|---|
| NHCO | 1 | 1 | $-CH_2NH(CO)CH_2NH_2$ | I-1 |
| NHCO | 0 | 0 | $-CH[(S)-CH_3]NHCOCH[(S)-CH_2CO_2H]NHCO-$ $CH_2NHCOCH[(S)-(CH_2)_3NH(C=NH)NH_2]NH_2$ | I-2 |
| NHCO | 1 | 0 | $-(CH_2)_6NHZ$ | I-3 |
| NHCO | 1 | 0 | $-(CH_2)_6NH_2$ | I-4 |
| O | 6 | 1 | $-CH(NHZ)(CH_2)_2COOBn$ | I-5 |
| O | 6 | 1 | $-CHNH_2(CH_2)_2COOH$ | I-6 |
| O | 6 | 1 | $-(CH_2)_2COOH$ | I-7 |
| O | 6 | 1 | $-CH(NHZ)CH_2OBn$ | I-8 |
| O | 6 | 1 |  | I-9 |
| O | 6 | 1 |  | I-10 |
| O | 6 | 1 |  | I-11 |

| Y | n | p | C(=O)-R² | (I) |
|---|---|---|---|---|
| O | 6 | 1 |  | I-12 |
| O | 6 | 1 |  | I-13 |
| O | 6 | 1 |  | I-14 |
| O | 6 | 1 |  | I-15 |

{ SLeX-Y(CH₂)ₙ[NH(CO)]ₚ(CH₂)ₘ-[NH(CO)]q-CH₂CH₂
SLeX-Y(CH₂)ₙ[NH(CO)]ₚ(CH₂)ₘ-[NH(CO)]q-CH₂CH₂ ⟩—NO₂   (II)
SLeX-Y(CH₂)ₙ[NH(CO)]ₚ(CH₂)ₘ-[NH(CO)]q-CH₂CH₂

| Y | n | p | m | q | (II) |
|---|---|---|---|---|------|
| NHCO | 0 | 0 | 0 | 0 | II-1 |
| O | 6 | 1 | 0 | 0 | II-2 |
| O | 6 | 1 | 6 | 1 | II-3 |

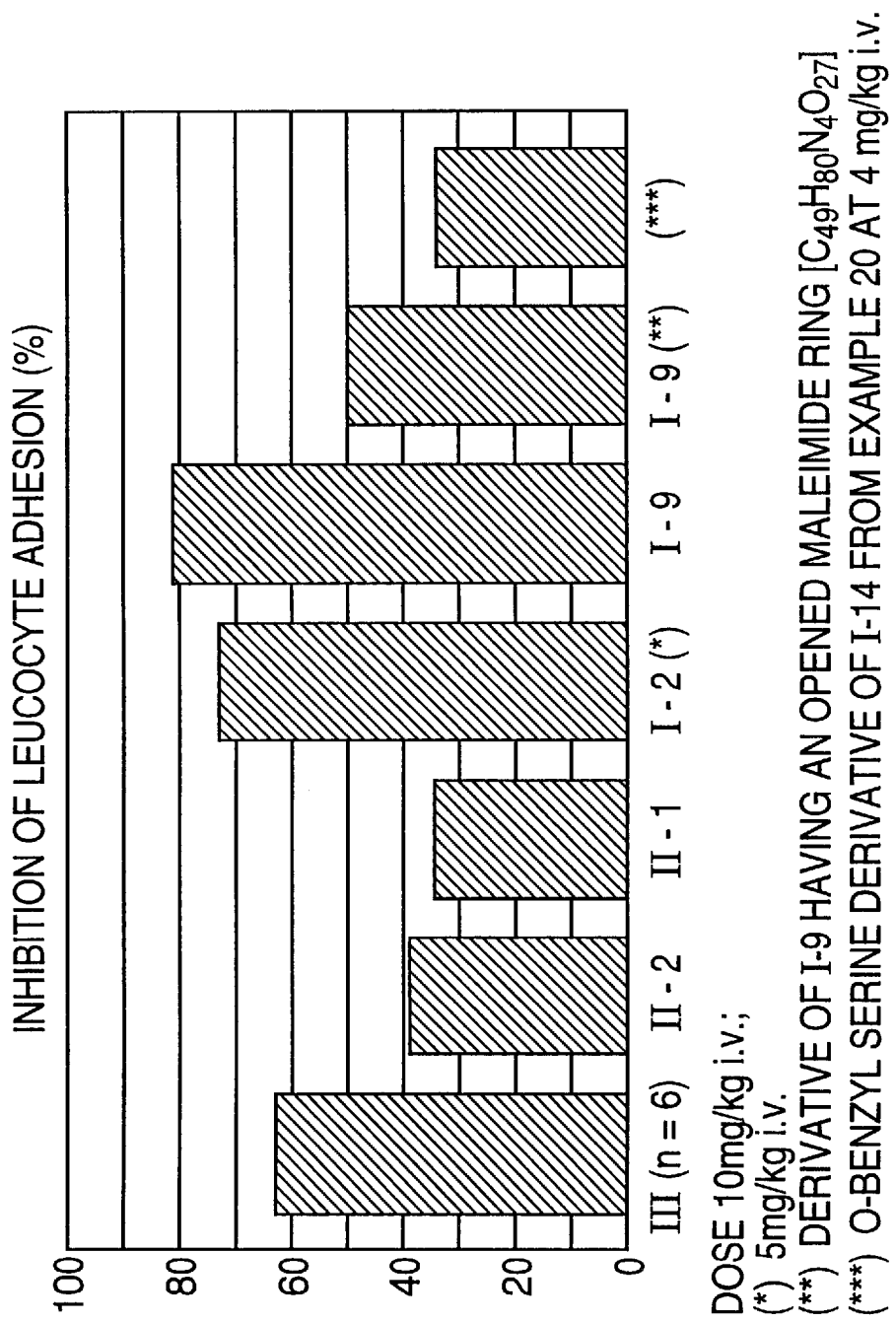

CARBOHYDRATE CONJUGATES AS INHIBITORS OF CELL ADHESION

BACKGROUND OF THE INVENTION

The invention relates to novel conjugates of tetrasaccharides, preferably of sialyl-Lewis X (SLeX) and sialyl-Lewis A (SLeA), with improved action as inhibitors of cell adhesion, a process for the preparation of these compounds, and their use as pharmacological active compounds and as diagnostics, and pharmaceuticals which contain these conjugates.

The circulation of blood cells, e.g. leucocytes, neutrophils, granulocytes and monocytes is, on a molecular plane, a multistage, very complex process which is only known in individual steps (Review: T. A. Springer, Cell 76, 301–314, 1994).

The most recent research results showed that the recirculation of the lymphocytes crucial in immune monitoring and the localization of neutrophils and monocytes at inflammatory foci respond to very similar molecular mechanisms. Thus in acute and chronic inflammatory processes adhesion of the leucocytes to endothelial cells and migration into the inflammatory focus and into the secondary lymphatic organs occurs.

This process involves numerous specific signal molecules, e.g. interleukins, leucotrienes and tumor necrosis factor (TNF), receptors coupled to their G protein and in particular tissue-specific cell adhesion molecules, which guarantee a specifically controlled recognition of the immune and endothelial cells. The most important adhesion molecules involved in this process, which in the following will be designated as receptors, include the selectins (E-, P- and L-selectins), integrins and the members of the immunoglobulin superfamily.

The three selectin receptors determine the starting phase of leucocyte adhesion. E-selectin is expressed on endothelial cells a few hours after stimulation, for example by interleukin-1 (IL-1) or tumor necrosis factor α (TNF-α), while P-selectin is stored in blood platelets and endothelial cells and is presented on the cell surfaces after stimulation by thrombin, peroxide radicals or substance P among others. L-selectin is continuously expressed on leucocytes.

It is today generally recognized that the tetrasaccharides sialyl-Lewis X (SLeX) and sialyl-Lewis A (SLeA) which occur on cell membranes as substructures of glycosphingolipids and glycoproteins, can function as ligands for all three selectin receptors. (Review: A. Giannis, Angew. Chem. 106, 188, 1994):

<u>Sialyl-Lewis X</u>

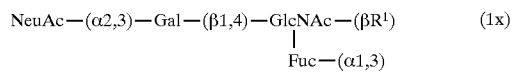

         SLeX—OH for $R^1$ = OH

<u>-continued</u>
<u>Sialyl-Lewis X</u>

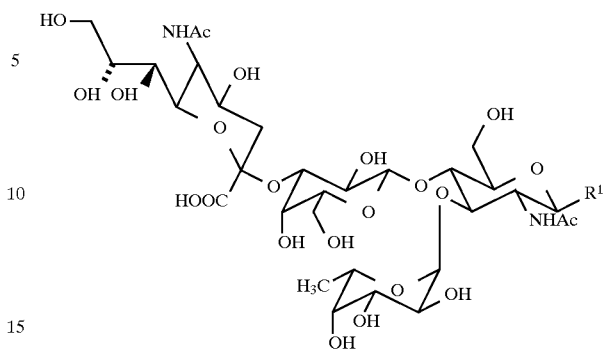

The regioisomeric compound sialyl-Lewis A is closely related to the X type and binds to selectin receptors with comparable affinity. The A type arises from the X type by simple exchange of the "side chains" on the central N-acetylglucosamine unit:

<u>Sialyl-Lewis A</u>

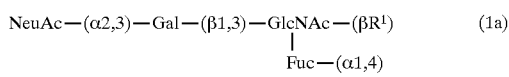 (1a)

         SLeA—OH for $R^1$ = OH

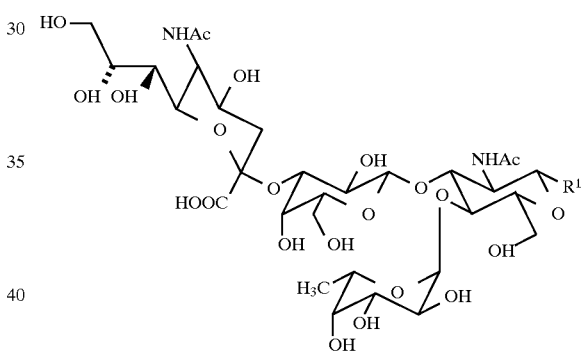

The course of a number of acute and chronic disorders is unfavorably affected by the excessive adhesion of leucocytes and their infiltration into the tissue affected. These include, for example, rheumatism, reperfusion injuries such as myocardial ischemia/infarct (MI), acute pneumonia after operative intervention, traumatic shock and stroke, psoriasis, dermatitis, ARDS (adult respiratory distress syndrome) and the restenosis occurring after surgical intervention (for example angioplasty).

A very promising therapeutic starting point is therefore the attempt to employ the tetrasaccharides SLeX/A in various administration forms or mimetics thereof having a modified structure as antagonists for the modulation or suppression of excessive leucocyte adhesion and to employ them for the alleviation or cure of said disorders.

The natural ligand having the structure of SLeX has already been successfully used in animal experiments in P-selectin-dependent lung injuries (M. S. Mulligan et al., Nature 1993, 364, 149) and in myocardial reperfusion injuries (M. Buerke et al., J. Clin. Invest. 1994, 93, 1140). In primary clinical trials in acute pneumonia the compound should be employed in a dose of 1 to 2 grams per day per patient (communication of Cytel Corp./La Jolla (CA.) in the 2nd Glycotechnology Meeting/CHI in La Jolla/USA on May 16–18th 1994). This high dose of active compound is in agreement with the, as is known, weak affinity of the natural SLeX/A ligands for the selectin receptors. Thus SLeX in all known in vitro test systems inhibits cell adhesion to selectin receptors only at a relatively high concentration in the range of $IC_{50}$=1 to 3 mM.

In some publications, meanwhile, efforts to obtain more strongly binding antagonists by structural variation of the ligand have been reported. The variation of the fucose and neuraminic acid units until now regarded as crucial for the structure-activity relationship (B. K. Brandley et al., Glycobiology 1993, 3, 633 and M. Yoshida et al., Glycoconjugate J. 1993, 10, 3), however, did not afford any significantly improved inhibition values. Only on variation of the glucosamine unit (replacement of GlcNAc by glucose and azido and amino groups in the 2-position of GlcNAc) could a significantly increased affinity to the E-selectin receptor be achieved. The $IC_{50}$ data of these compounds which can be prepared by complete de novo synthesis should be 0.12 mM (compared with 1.2 to 2.0 mM for SLeX) for the inhibition of the adhesion of HL-60 and U-937 cells with E-selectin. A disadvantage, however, is that the binding to L- and P-selectins at >5 mM is severely impaired (Dasgupta et al., poster presentation of Glycomed Inc. on the occasion of the conference in La Jolla in 5/94).

In another in vitro test system, in which, with reversal of the natural physiological conditions, the soluble receptor construct E-selectin-IgG (instead of the corresponding receptor construct in immobilized form, which would more likely be comparable with the natural situation on endothelial cells) binds to the immobilized ligands and is displaced by potential inhibitors, in the system E-selectin-IgG/immobilized BSA-SLeA a 36-fold higher affinity was found for the ligand with N-acetyl-glucosamine deacetylated in the 2-position.

Apart from a restricted comparability of this artificial test system with the situation in vivo, i.e. the inhibition of the adhesion of cells which express the natural ligands SLeX/A, this result remains restricted to the E-selectin receptor, for with the P-selectin receptor only weak inhibition effects were found at inhibitor concentrations of about 1 mM (R. M. Nelson et al., J. Clin. Invest. 1993, 91, 1157).

The prior art on the binding affinity of modified SLeX/A structures to selectins is referred to in Pharmacochem. Libr. 1993, 20 (Trends in Drug Research), pages 33–40.

Modified ligands of the SLeX/A structural type, which are mainly derived from the lactose and from the lactosamine basic structure and could be employed, inter alia, as potential selectin antagonists, are claimed in several patent applications, in particular in the international publications
WO 91/19501, WO 91/19502, WO 92/02527, WO 93/10796,
WO 94/00477, WO 92/18610, WO 92/09293, WO 92/07572,
WO 92/16640, WO 92/19632, WO 93/17033, WO 93/23031,
WO 92/22301, WO 92/22563, WO 92/22564, WO 92/22565,
WO 92/22661, WO 92/22662, WO 93/24505, WO 93/24506.

SLeX/A derivatives or mimetics having clearly improved affinity for the E-selectin and for the P-selectin receptor in vitro have still not been described. What are remarkable, however, are indications that multivalent ligands could have a higher binding affinity compared with monovalent ligands: thus an enzymatically prepared, complex nonasaccharide binds 5 times better ($IC_{50}$=0.4 mM) to E-selectin as a potentially divalent ligand than the monomeric SLeX ligand. On closer analysis, this value, however, does not represent a convincing multivalent effect: if it is considered that the $IC_{50}$ value calculated per ligand is actually only 0.8 mM, then no significant improvement was actually achieved (S. A. DeFrees et al., J. Am. Chem. Soc. 1993, 115, 7549).

A further possibility for the multiple presentation of the SLeX/A ligands consists in the introduction of (co) polymerizable side chains or in the binding of a suitable SLeX precursor to a multifunctional polymer. The first variant leads to artificial polymer conjugates, for example to polyacrylamides, which are unsuitable as pharmaceuticals on account of their physiological intolerability. In the literature, this procedure was described for polyacrylamide conjugates of the Lewis X trisaccharide (S.-I. Nishimura et al., Macromolecules 1994, 27, 157). The process can also be applied to SLeX, SLeA and analogs in which the sialic acid has been replaced by sulfate (E. Nifantév, Lecture, Glycotechnology Meeting, La Jolla, May 16th–18th, 1994).

The second variant, in which SLeX derivatives are reacted with a reactive polymer to give multifunctional, biocompatible and physiologically tolerable polymer conjugates, is described in EP 0 601 417. In this publication reference is also made in detail to the prior art on carbohydrate polymer conjugates.

An inherent disadvantage of these carbohydrate polymer conjugates with respect to their utility as pharmaceuticals lies in the polymer nature of active compounds of this type: in each synthetic batch a new type of product is obtained which is characterized by a differing molecular weight distribution and by a variable coating density of the carbohydrate ligand bound to the polymer.

In WO 94/00477, it is proposed to prepare multivalent compounds by reductive amination of the oxime adducts of ligands of the structural type (1), which are present as free oligosaccharides (i.e. $R^1$=OH), with peptides or proteins. This process, however, has serious disadvantages, as the SLeX ligand is severely modified by the ring opening of the first carbohydrate unit at the reducing end (GlcNAc or Glc). Additionally, as in the polymer conjugates mentioned, only inexactly defined and uncharacterizable mixtures are to be expected. This is shown plainly in the example described hypothetically in WO 94/00477, in which using a 10,000-fold excess (1 mmol) of useful oligosaccharide a coupling to the tripeptide Lys-Tyr-Lys on the analytical scale of 0.1 μmol of Lys-Tyr-Lys tripeptide is proposed. After carrying out analytical separation processes, the possibility of an analysis by means of mass spectroscopy is mentioned, according to which mixtures of mono-, di- and trivalent carbohydrate conjugates are expected.

Low molecular weight compounds are therefore desirable having an unequivocal empirical formula and defined molecular weight and having a distinctly increased receptor affinity. Compounds are particularly desirable which simultaneously meet all the requirements mentioned and moreover can be prepared on the preparative scale (gram amounts) in efficient synthetic processes.

The object of the invention is to provide low molecular weight carbohydrate receptor blockers, a simple process for their preparation, and pharmaceuticals prepared from these which meet the requirements mentioned.

This object is achieved according to the invention by the simple coupling of oligosaccharides which can be carried out in a few steps and in high yields, preferably with SLeX/A structures, to mono- and trifunctional precursors to give novel carbohydrate conjugates. The useful oligosaccharide component can be employed stoichiometrically or in a small excess of 1 to 10 mol % per active group and preferably in unprotected form.

Surprisingly, in the synthetic route according to the invention to trivalent carbohydrate conjugates, only small amounts of the divalent by-products are formed, which can be separated off easily from the desired main products.

The finding is additionally surprising that the novel conjugates bind to E- and P-selectins more strongly than the natural ligand of the formula (1). The agonistic and antagonistic action of the compounds according to the invention can be employed for the prophylaxis, therapy and diagnosis of disorders which are characterized by excessive cell-cell adhesion.

SUMMARY OF THE INVENTION

The invention thus relates to a compound of the formula 1, $$Z-Y-(CH_2)_n-[NH(CO)]_p-R^2 \qquad 1,$$

in which

Z is a branched tetrasaccharide,

Y is oxygen or NH(CO) and $R^2$ is an amino acid or oligopeptide radical of up to 6 amino acids,
a lipophilic radical formed from aliphatic or cycloaliphatic units,
a combination of aliphatic and heterocyclic units or
a triphenylmethane dye, where for Y=oxygen p is 1 and n is an integer from 2 to 10, and for Y=NH(CO) and p=0 n is an integer from 0 to 10, and for Y=NH(CO) and p=1, n is an integer from 1 to 10.

Preferably the branched tetrasaccharide Z is sialyl-Lewis X or sialyl-Lewis A.

Preferably, $R^2$ is a group of the formula (1A),

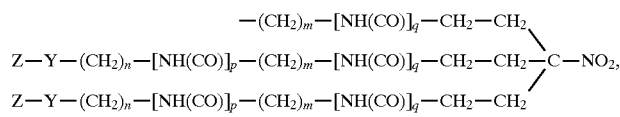

where m is an integer from 0 to 10 and p and q can be 0 or 1, with the proviso that for m=0 either p or q is equal to 0.

These preferred embodiments of compound (I) (where $R^2$=1A) are given in the following compound (II)

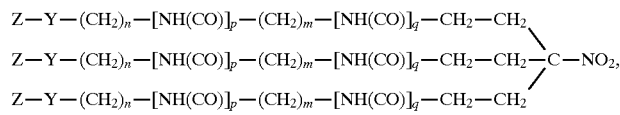

The present invention further relates to a process for the preparation of a compound (I), which is distinguished in that a compound of the formula (III)

$$Z-O-(CH_2)_n-NH_2 \qquad III,$$

a compound of the formula (IV), $$Z-NH_2 \qquad IV$$

or a compound of the formula (V)

$$Z-NH(CO)-(CH_2)_n-NH_2 \qquad V$$

in which Z and n have the meanings mentioned, is reacted with a compound of the formula (VI)

$$X(CO)R^2 \qquad VI$$

in which

X is hydroxyl or a carboxyl-activating leaving group and $R^2$ has the meanings mentioned, the branched tetrasaccharide Z of the precursors (III), (IV) or (V) in some cases being employed in protected form, but preferably in unprotected form.

X in compound (IV) is preferably an O-succinimidyl group.

The solvent employed for this reaction is preferably pyridine or N,N-dimethylformamide.

Advantageously, for the preparation of a compound of the formula (I) in which the branched tetrasaccharide Z is sialyl-Lewis X or sialyl-Lewis A, the sialic acid radical in the tetrasaccharide radical Z of precursor (III), (IV) or (V) is present in the lactone form.

To prepare a compound of the formula (II), $R^2$ in precursor (VI) is suitably a group of the formula (IB)

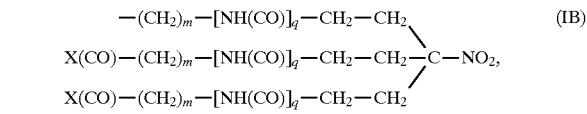

or a compound of the formula (VII)

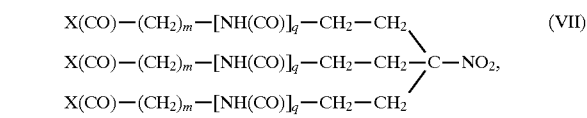

is used as a suitable precursor, the variables m and q having the meanings already mentioned.

The present invention further relates to a pharmaceutical containing a compound of the formula (I) and, if appropriate, pharmaceutical auxiliaries.

The compound of the formula (I) can in particular be used for the preparation of a pharmaceutical for the prevention or cure of diseases which are caused by increased cell-cell adhesion.

The compound (I) is further suitable for the production of a composition for the diagnosis of diseases which accompany increased cell-cell adhesion and for the preparation of a synthetic vaccine.

BRIEF DESCRIPTION OF THE DRAWINGS

FIG. 8 shows the in vivo leucocyte adhesion assay results from example 31.

DETAILED DESCRIPTION OF THE PREFERRED EMBODIMENTS

Figure 1:
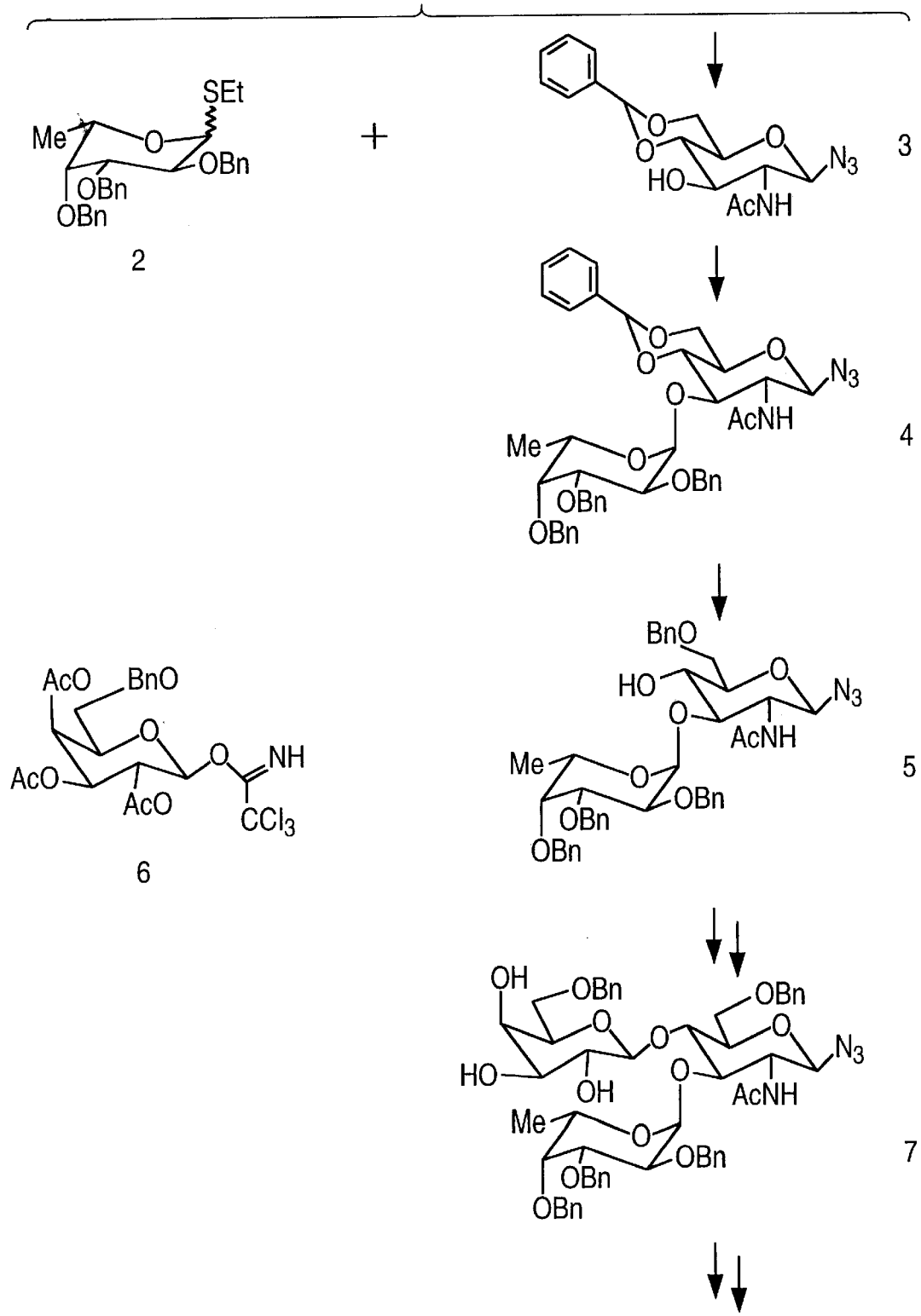
FIG. 1 shows a synthesis of 1-azido-1-deoxy-LeX-trisaccharide (Bn=benxyl).

In the following, the invention is described in detail, in particular in its preferred embodiments. The invention is furthermore determined by the contents of the patent claims.

Synthesis of the compounds (I) having an O-glycosidic bond (Y=O)

The compounds of the formula (I)

$$Z—Y—(CH_2)_n—[NH(CO)]_p—R^2 \qquad I$$

in which the carbohydrate ligand Z, which preferably contains an SLeX or SLeA structure, is linked O-glycosidically (i.e. Y=O) and optionally via an aliphatic spacer chain $(CH_2)_n$ to amino acids, peptides or further lipophilic radicals $R^2$, can be prepared from precursors of the formula (III) known from the literature in a simple manner by direct coupling of the reagents of the formula (VI), optionally protected in the secondary functionalities, and subsequent removal of protective groups.

Examples of suitable syntheses of the oligosaccharide precursors (III) are found in EP 0 601 117 and in Angew. Chem. probably Issue 19, 1994 (in press), for compounds where n=6 (hexanolamine spacer), in J. Carbohydr. Chem. 1993, 1, 1203 (n=2 and n=8) and in J. Carbohydr. Chem. 1994, 13, 641 (sialyl-Lewis A type). In the compounds mentioned in the publication mentioned last but one, the amino function can be introduced by reduction of the azide precursor by processes familiar to the person skilled in the art. Accordingly, the replacement of every third methylene unit in the spacer chain $(CH_2)_n$ of compounds of the formula (III) by oxygen atoms with the aim of a better water solubility and bioavailability of the desired final products (I) is likewise possible.

Suitable acyl components (VI) are aliphatic or cycloaliphatic carboxylic acids and amino acids, and peptides with up to 6 amino acids having a free acid function (X=OH), which are protected at the N terminal and in the amino and carboxyl side-chain functions and can react with the primary amino function of the precursor (III) with the formation of an amide bond. With respect to the selection of suitable compounds (VI) where X=OH, restrictions hardly exist on account of the high reactivity and good accessibility of the amino function. For linkage of the peptide bond, the customary processes of peptide synthesis with in situ activation of the acid function, for example with carbodiimides, can be used. A compilation of all customary processes is found in "Principles of Peptide Synthesis", M. Bodanszky, 2nd Edition 1993, Springer-Verlag.

On account of the presence of a free acid function and numerous hydroxyl groups in the carbohydrate units having SLeX and SLeA structure, these methods are less suitable, however, because of possible side reactions. In a preferred embodiment, the unprotected carbohydrate precursors (III, IV, V) are reacted with the pure active esters (VI) in order to guarantee an unequivocal reaction course.

Examples of suitable active esters which are either commercially available or can be prepared by the processes cited in the text book about peptide syntheses by M. Bodanszky (see above) are pentafluorophenyl esters (X=pentafluorophenoxy), 2,4-dinitrophenyl esters (X=2,4-dinitrophenoxy) and O-acylated, substituted hydroxylamines such as, for example, N-hydroxysuccinimide esters (X=OSu), which are employed in a particularly preferred embodiment.

A particular difficulty in carrying out reactions of unprotected carbohydrate precursors such as III (and also IV and V) is the high hydrophilicity of the compounds in comparison with the more strongly hydrophobic active esters (VI), which counteracts efficient reaction of the components in the customary organic solvents, in aqueous systems or in solvent mixtures. In the embodiment according to the invention, the reaction is carried out at 0° to 100° C., preferably at temperatures around room temperature of 15° to 35° C. in solvents such as DMF, dimethyl sulfoxide, or pyridine, preferably in pyridine.

The unprotected compounds (III) which are soluble to a small extent in pyridine, but sufficiently for complete reaction within 1 to 24 hours with good stirring and adequate dilution, are preferably reacted. The lactone SLeX and SLeA compounds, which formally can be formed by removal of a water molecule, are particularly preferred. These compounds are obtained at the end of the synthesis sequence for the precursors as regioisomeric mixtures after removal of the protective groups (Example: J. Chem. Soc., Chem. Commun. 1991, 870). It was found that these SLeX/A lactones are substantially more soluble in organic solvents, in particular in pyridine, and are thus ideal precursors for the synthesis process according to the invention. The free carboxyl group of the sialic acid can then be liberated simply under mild basic hydrolysis from the lactone group in the last synthesis step.

Further protective groups present in the peptide radicals $R^2$ of the products (I) are removed by the customary processes, for example benzyl radicals in esters or ethers by catalytic hydrogenation and FMOC protective groups of amines under mild basic hydrolysis. The methods are described, for example, in the text book by Bodanszky (see above) and in "Protective Groups in Organic Synthesis" (Th. W. Greene, J. Wiley & Sons, 1981).

Protective groups which have to be removed under strongly acidic conditions, e.g. hydrochloric acid or trifluoroacetic acid, are not suitable on account of the acid sensitivity of the compounds. The final compounds are isolated and purified by removal of the solvent and by means of chromatographic methods such as HPLC or FPLC, preferably by gel permeation chromatography on support phases such as e.g. Biogel™ or chromatography on Sephadex™ using water or water/alcohol mixtures. The compounds are characterized by thin-layer chromatography on silica gels, electrospray or FAB mass spectrometry, nuclear magnetic resonance spectroscopy and biological assay systems to test for inhibition of cell adhesion to selectin receptors.

Synthesis of the compounds (I) having an N-glycosidic bond (Y=NHCO)

The compounds of the formula (I)

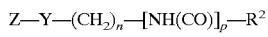

in which the carbohydrate ligand Z, which preferably has an SLeX or an SLeA structure, is N-glycosidically acylated, where Y is the amide group NH(CO), p=0 and n=0, are prepared from the β-glycosylamine (IV) by acylation with a compound (VI) in a completely analogous manner to that described above. The glycosylamine precursors (IV) can be prepared in principle from SLeX or SLeA by ammonolysis of the free saccharides according to known processes, for example by reaction of the compounds (1x) or (1a) with ammonium hydrogen carbonate in water according to the process customary for free saccharides (Glycoconjugate J. 1993, 10, 227 and EP 0 413 675).

EP 0 413 675 also describes, for example, the acylation of the glycosylamines prepared by this process with chloroacetic acid derivatives, which are further reacted with linkers and fluorophoric groups, in particular for analytical applications. Acylation is carried out using very large excesses of reagent (5 molar excesses) on the micro scale and is at the most suitable for the preparative synthesis with useful components of the formulae (IV) and (VI) to give the products (I) on the gram scale because of the lability of the free glycosylamines in the aqueous reaction medium and in water/DMF mixtures, but unsuitable for the synthesis on large scale.

In a preferred embodiment for the acylation of the glycosylamines (IV), precursors, which are protected in some cases, of the oligosaccharides having SLeA or SLeX structure are employed whose synthesis is shown in schemes 1 to 3 as exemplified by the SLeX-glycosylamine precursor and is described in detail in the examples: the selectively protected N-acetylglucosamine compound (3) is fucosylated using the thioglycoside donor (2) to give (4). The disaccharide (4) is reduced with sodium cyanoborohydride/hydrochloric acid in THF (Garegg method) to give the intermediate product (5) from which after galactosylation with the donor (6) and deacetylation according to the Zemplen method the trisaccharide (7) is obtained (see scheme shown is FIG. 1).

From the trisaccharide (7), a mixture of the methyl ester (10) and of the 4'-lactone (9) is formed by reaction with sialic acid donor (8) according to the thioglycoside method and transesterification with sodium methoxide. Both compounds can further be converted into the final products by the same process. According to the scheme shown in FIG. 2, the tetrasaccharide lactone (9) is selectively reduced on the anomeric azide group using Raney nickel to give the partly protected glycosylamine (11). Compound (11) represents an example of a partly protected precursor of the formula (IV) containing the tetrasaccharide ligand in the sialyl-Lewis X configuration. Alternatively, the benzyl protective groups can additionally be removed reductively using palladium/hydrogen. In both cases, the amino group of β-configuration is formed in selectively acylatable form.

However, the first variant of a use of the partly protected glycosylamines in the embodiment preferred according to the invention offers the advantage that, for the subsequent acylation with the reaction components (VI), compounds having comparable hydrophobicity in organic solvents such as, for example, pyridine, dichloromethane, dimethylformamide (DMF), acetonitrile, tetrahydrofuran (THF) or mixtures thereof can be used. In the example according to the scheme shown in FIG. 3, the Z-protected succinimide ester of the tripeptide Gly-Gly-Gly (12) with the partly protected glycosylamine (11) is reacted in a dimethylformamide/dichloromethane mixture to give the glycopeptide (13), from which, after reductive removal of the protective groups, the 4'-lactoid form (14) of a final product of the formula (I) is obtained. The tetrasaccharide glycopeptide having a free carboxyl function on the sialic acid, in the example the final compound (I-1), is obtained by mild hydrolysis of the lactone ring with dilute aqueous bases, for example with 0.1 to 0.01N sodium hydroxide solution, and subsequent acidification.

The compounds (I) having the sialyl-Lewis A configuration are obtained completely analogously to the manner described above: the compounds of this structural type are formed by exchange of the glycosylation components in the addition of the side arm in the 3- and 4-positions of the N-acetylglucosamine unit. Thus, in analogy to the schemes shown in FIGS. 1 and 2, galactosylation first takes place in the free 3-position and then, after reductive opening of the benzylidene acetal, fucosylation takes place in the free 4-position. Further synthesis proceeds completely analogously to the process described for (I-1).

The coupling of compounds of the formula (VI) to glycosylamines (IV) via succinimide active esters (I; X=OSu) is here also the preferred embodiment of the invention. The only secondary component of this reaction is the inevitably obtained N-hydroxysuccinimide. As otherwise no further reagents or activators are needed, the final products can be purified by simple filtration through stationary chromatography phases such as, for example, Biogel® using water as eluent or on Sephadex® or materials of similar type by means of water or mixtures of water with organic solvents as eluents. The reaction components of the formulae (IV) and (VI) are employed stoichiometrically or in excesses of 1 to 10 mol % of the component which is in each case available in a greater amount. The respective excess component is separated off after said chromatography processes.

The succinimide esters (VI) can be obtained in isolated form (X=OSu) or in situ from the carboxylic acids (VI, X=OH) using the commercially available reagent TSTU [O-(N-succinimidyl)-N,N,N',N'-tetramethyluronium tetrafluoroborate] or by other familiar processes of peptide synthesis (see cited ref.: M. Bodanszky). Thus, HOBT esters (HOBT=1-hydroxybenzotriazolyl), which are prepared in situ from carboxylic acids, or other special processes which have been developed specially for the acylation of chemically labile glycosylamines, can also be employed. An example of the latter is the use of 3-acyl-5-methyl-1,3,4-thiadiazole-2(3H)-thiones (J. Carbohydr. Chem. 1994, 13, 737).

In the preferred succinimide ester process according to the invention for the synthesis of the products (I) and (II), in contrast to the processes known from the literature, for example the HBTU process (Glycoconjugate J. 1993, 10, 227) for the acylation of free glycosylamines, the tetrasaccharide precursors (III), (IV) and (V) can also be used in the free sialic acid form. Preferably, however, the compounds present in the lactone form are employed.

The methods described and claimed in U.S. Pat. No. 5,280,113 for the coupling of peptides which consist of 5 to 25 amino acids to unprotected glycosylamines are not applicable to sialic acid-containing glycosylamines (IV). Thus, the activation of a carboxylic acid (VI, X=OH), for example by means of HBTU/HOBT would inevitably also lead to an activation of the sialic acid and thus to a different reaction course.

The characterization of the products is carried out in the same manner as mentioned above for the O-glycosides of the formula (I).

The compounds of the formula (I) in which the ligand having SLeX or having SLeA structure is likewise present in N-glycosidically acylated form (Y=NHCO), but p=1 and (CH$_2$), is an aliphatic spacer chain where n=1 to 10 carbon atoms, are prepared by acylation of appropriate precursors of the formula (V) completely analogously to the compounds (I) which can be prepared from precursors (III) (see above).

The precursors of the formula (V) are for their part prepared from the precursors (IV) using the corresponding processes described above, by acylation with terminal aminocarboxylic acids protected at the N terminus or their active esters. Examples of suitable terminal amino carboxylic acids are glycine (n=1) and 6-aminocaproic acid (n=6). Suitable protective groups for the N-terminal amino group are the hydrogenolytically removable azido and benzyloxycarbonyl (Z) protective groups and the trifluoroacetyl and fluorenylmethoxy-carbonyl protective groups (FMOC) which can be removed under mild basic conditions.

Figure 3:
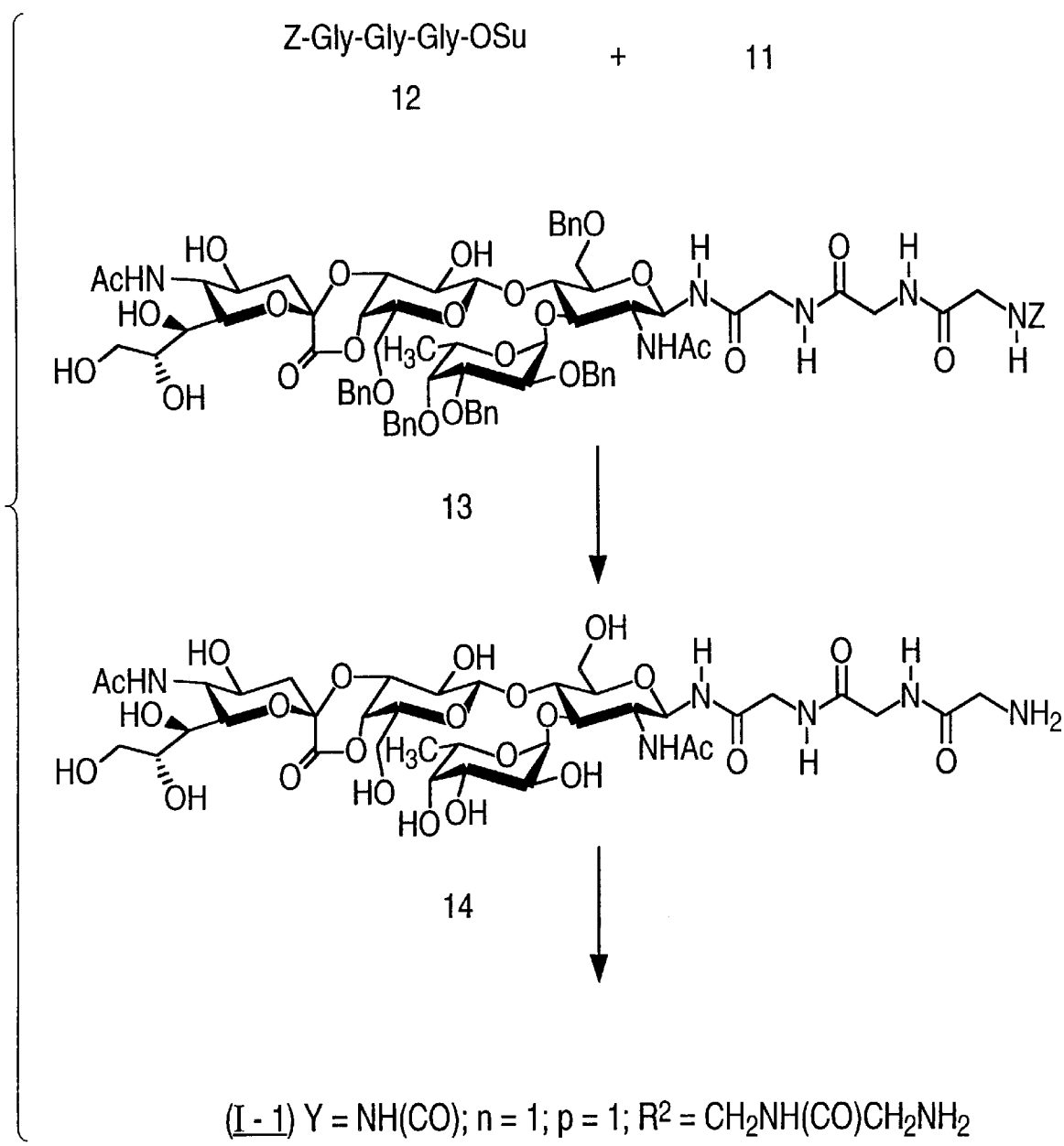
FIG. 3 shows a synthesis of sialyl-LeX-1-deoxy-1-aminoglycyl-Gly-Gly-Glycotripeptide (I).

Thus, when using SuO(CO) (CH$_2$)$_6$NH—Z, for example in analogy to the synthesis sequence described in the scheme shown in FIG. 3, the compound (V) where n=6 is obtained after removal of the Z protective group.

The process according to the invention for the synthesis of the carbohydrate conjugates (I) has in its preferred embodiment, the reaction of amino-functionalized carbohydrate precursors (III, IV or V) with the compounds (VI, X=OSu), the advantage that a great variety of carboxylic acids, amino acids and peptides having a free carboxylic acid function, which can all be converted to their OSu esters, can be used.

Figure 4:
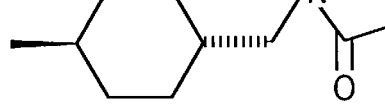
FIG. 4 are examples of compounds SLeX/A-Y$(CH_2)_n$[NH(CO)$]_p R^2$ (I).
Figure 4:
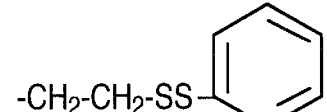
Figure 4:
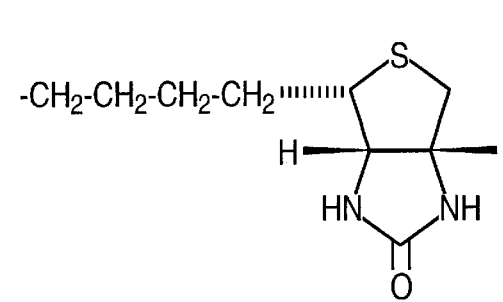

In FIG. 4 are shown examples of compounds obtainable in this way, which are intended to serve to illustrate the invention and the applications afforded by the diverse variability of radical R$^2$. The compounds (I) are especially also distinguished by their increased affinity for selectin receptors.

A further variant of the process according to the invention for the synthesis of novel lipophilic oligosaccharide ligands from the amino-functionalized carbohydrate precursors (III), (IV) or (V) is the addition of suitable isocyanates or isothiocyanates as reactive carboxyl components alternatively to the active esters of the formula (VI). In this case, products of the formula (I) are formed with (thio)urea bonds NH(CO)NH or NH(CS)NH instead of amide bonds, which hardly causes differences in the affinity of the compounds for the selectin receptors. An example of this is the synthesis of (I-16) shown in FIG. 6 by reaction of a precursor of the formula (III-1) with the commercially available reagent fluorescein isothiocyanate in pyridine as a solvent.

The fluorophoric compound (1–16) which can easily be prepared on the gram scale is particularly highly suitable, just like the compound obtainable completely analogously from the corresponding precursor having sialyl-Lewis A configuration, for in vitro and in vivo studies of cell adhesion. These compounds are better suited due to their optimal spacer length than the commercially available compounds of the company Oxford Glycosystems (Catalogue No. F-02026 and F-02028), in which the fluorophoric dye was coupled to the oligosaccharides via the rigid, short glycyl spacer. The more flexible spacer in (I-16) presents the carbohydrate ligand free from interfering effects of the relatively large dye molecule. This is shown by the IC$_{50}$ data (Table 1) which are further distinctly improved in comparison with the free sialyl-Lewis X tetrasaccharide (IC$_{50}$ values 1 to 2 mM) in (I-16).

The glycoconjugate (1–2) contains the antiadhesive peptide sequence Arg-Gly-Asp-Ala, which can additionally function as a binding site for integrins, for example for the glycoprotein GP IIb/IIIa. The peptide Arg-Gly-Asp-Ala on its own does not bind to selecting.

The biotin glycoconjugate (I-11) forms addition compounds with avidin and with streptavidin, in which up to 4 sialyl-Lewis X ligands are bonded.

The glycoconjugate (I-12) contains the structural element of the chemotactic peptide N-formyl-Met-Leu-Phe (fMLP), of which a synergistic effect is to be expected in vivo with respect to reduced rolling of neutrophils (Blood 1993, 82, 1165–1174).

The glycoconjugates (I-13) and (I-14) contain the structural element of lipopeptide vaccines of the Pam$_3$Cys(Ser) type. In contrast to peptides, lipopeptides having this structural element cause a primary immune response to an antigen stimulus by being rapidly transported through cell membranes and then internalized in the cytoplasm. This process leads to the activation of macrophages and to an antigen-specific immune response.

The T-cell-mediated immune response to proteins is a known mechanism in tumor research, while here there is still no knowledge about the role of carbohydrates. A prerequisite for this process is the presentation of peptides which bind to MHC proteins. WO 93/21948 proposes immunogenic conjugates for the generation of T-cell-mediated immunity against tumor-associated carbohydrate antigens which contain MHC-1 binding peptides and an immunogenic carbohydrate ligand.

On the other hand, as potential synthetic vaccines a specific immune response is to be expected from the compounds (I-13) and (I-14) to the sialyl-Lewis X antigen, which can also be induced independently of the MHC mechanism. The same applies to the compound obtainable in an analogous manner having a sialyl-Lewis A ligand structure. In inflammatory diseases and autoimmune diseases without the aid of macromolecular carriers or adjuvants, the immune response could lead indirectly to decreased leucocyte adhesion and infiltration by reducing the number of available antigen ligands.

This concept is an extension of the known strategy in antitumor therapy of use of synthetic, low molecular weight lipopeptide tumor antigen conjugates, which was reported on for the first time in J. Am. Chem. Soc. 1994, 116, p. 395. In comparison with the glycoconjugates of the Tn antigen type used there, the compounds (I-13) and (I-14) according to the invention are better suited for the induction of an immune response on account of their larger carbohydrate structures. A reinforcement of the immune response with participation of T cells can likewise be expected.

Synthesis of the compounds (II)

The compounds of the formula (I),

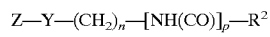

in which R$^2$ is a group of the formula (1A),

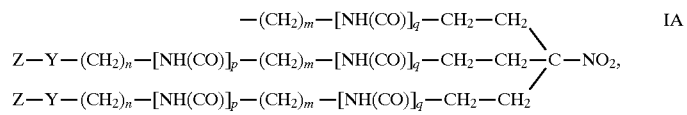

are given in the following compounds of the formula (II),

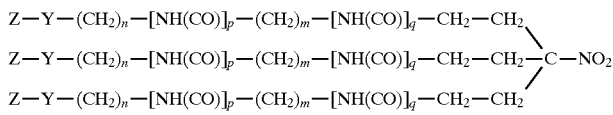

II

The compounds (II), in which three carbohydrate ligands Z, which preferably have an SLeX or SLeA structure, are present N- glycosidically or O-glycosidically acylated and, optionally extended via the aliphatic spacer chains $(CH_2)_n$ and $(CH_2)_m$, coupled via amide bonds to the skeleton compound 4-(2-carboxyethyl)-4-nitroheptanedioic acid (VII-1, X=OH, m=q=0), are prepared by triple reaction in each case of a compound of the formula (III), (IV) or (V) with the compound (VII-1) or with a chain-extended derivative of the formula (VII)

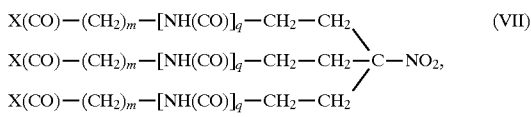

(VII)

Fundamentally, the methods employed for the synthesis of compounds (I) having a monovalent carbohydrate structure can also be used here for the linkage of amide bonds. Owing to the trivalent nature of a compound of the formula (VII), in this case, however, barely separable mixtures of mono-, di- and trivalent products are obtained. In the preferred embodiment of the invention, in which gram amounts of defined trivalent products (II) can easily be prepared, the novel (not yet described) tris-OSu esters of (VII, X=OSu) are used which are synthesized from the commercially available tricarboxylic acid (VII-1) as illustrated in the following examples (Su=succinimidyl radical):

example to the precursor (VII-1), and subsequent coupling with (III), (IV) or (V) as shown or alternatively by changing the synthetic sequence by coupling the amino acid protected on the amino group first to (III), (IV) or (V) and then adding the intermediate three times to the tris-OSu ester of a skeleton compound (VII) after deprotecting the amino group.

The first alternative is to be preferred, as the more valuable compound (III), (IV) or (V) is employed only in the last step.

Carrying out the synthesis of a compound (II), purification of the products and characterization thereof take place completely analogously to the manner described for the monovalent compounds (I).

Per reactive group-of (VII), the compound (III), (IV) or (V) is employed in at most 1 to 10 mol % excess.

The nitro group present in the compounds (II) can be reduced to the amino group by processes familiar to the person skilled in the art, for example using Raney nickel and hydrogen. The same final compounds containing an amino group could fundamentally also be prepared starting from the commercially available compound 4-(2-carboxyethyl)-4-aminoheptanedioic acid. For this, however, the roundabout route via the introduction of a suitable amino protective group would have to be selected, only amino protective groups which can be removed basically or hydrogenolytically being suitable. A Boc protective group which can be removed acidolytically would in no case lead to the products

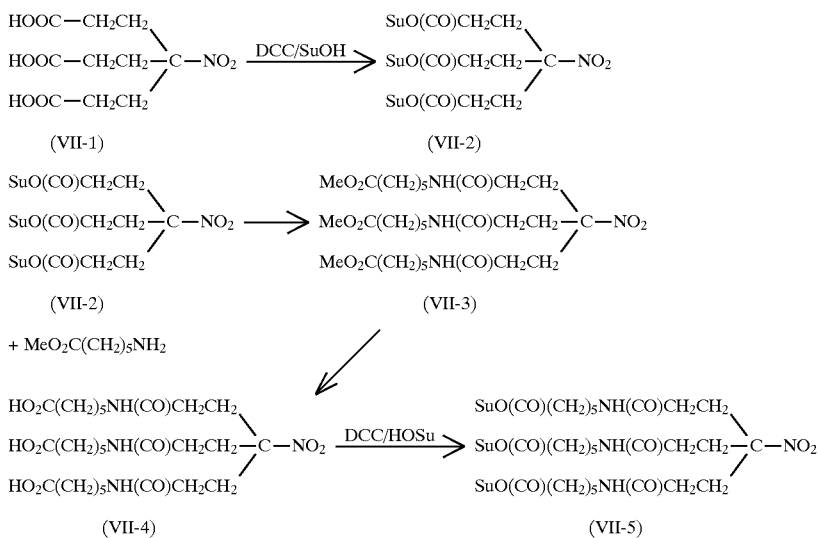

Examples of compounds (II) prepared in this way are found in Scheme 5. For example, the compound (II-1) is obtained by reaction of (VII-2) with at least three equivalents of a compound (IV) having the SLeX configuration. The compound (II-2) is formed in an analogous manner from a precursor (III) in which n=6. The compound (II-3) is obtained, for example, from (VII-5) and the compound (IV) having an SLeX configuration.

Trivalent products derived from a compound (III), (IV) or (V) can be prepared either by linkage of spacer chains, for corresponding to the formula (II) (having an amino group instead of the nitro group), as under these conditions the fucose would likewise be removed.

The synthesis concept for polyvalent compounds of the compounds (II) type is not restricted to trivalent glycoconjugates. Higher valent glycoconjugates, for example tetravalent compounds, can be prepared in an analogous manner from the corresponding oligocarboxylic acids, for example from 2,2'-bis (2-carboxyethyl)pentanedioic acid, to be specific likewise preferably via their N-hydroxy-succinimide esters.

Properties of the compounds (I) and (II) according to the invention as inhibitors of cell adhesion, and their therapeutic and diagnostic use.

The compounds of the formulae (I) and (II) are suitable as pharmacologically active substances, in particular as active compounds for the prophylaxis or cure of diseases which are caused by increased cell-cell adhesion. The compounds according to the invention in particular show improved efficacy in the inhibition of cell adhesion mediated by selectin receptors.

The carbohydrate conjugates must have no disadvantageous side effects in applications in vivo. Thus, in the case of intravenous administrations, hemolytic and undesired immunogenic properties, for example, are to be avoided. The enzymes of the blood clotting cascade must not be activated, in order to exclude the formation of thrombi.

The carbohydrate conjugates according to the invention and their physiologically tolerable salts are very highly suitable on account of their valuable pharmacological properties for use as therapeutics in mammals, in particular man. The pharmaceuticals are preferably suitable for the prophylaxis and/or therapy of diseases which proceed with involvement of inflammatory processes, preferably of myocardial infarct and ischemia, post-infarct syndrome, shock lung of the adult, septic shock, stroke, acute and chronic organ rejection, vasculitis, inflammatory diseases of the skin, rheumatoid arthritis, restenosis after angioplasty and also metastasizing tumors.

The pharmaceuticals according to the invention are in general administered intravenously, orally or parenterally or as implants, but rectal application is also possible in principle. Suitable solid or liquid pharmaceutical preparation forms are, for example, granules, powders, tablets, coated tablets, (micro)capsules, suppositories, syrups, emulsions, suspensions, aerosols, drops or injectable solutions in ampoule form and also preparations having protracted release of active compound, in whose preparation excipients and additives and/or auxiliaries such as disintegrants, binders, coating agents, swelling agents, glidants or lubricants, flavorings, sweeteners or solubilizers are customarily used. Frequently used excipients or auxiliaries which may be mentioned are e.g. magnesium carbonate, titanium dioxide, lactose, mannitol and other sugars, talc, lactoprotein, gelatin, starch, vitamins, cellulose and its derivatives, animal and vegetable oils, polyethylene glycols and solvents, such as, for example, sterile water, alcohols, glycerol and polyhydric alcohols.

The pharmaceutical preparations are preferably prepared and administered in dose units. In the case of solid dose units, tablets, capsules and suppositories are preferred.

For treatment of a patient, different daily doses are necessary depending on the efficacy of the compound, manner of administration, nature and severity of the disease, and age and body weight of the patient. Under certain circumstances, however, higher or lower daily doses may also be appropriate. The daily dose can be administered both by single administration in the form of an individual dose unit or else as several small dose units and also by multiple administration of subdivided doses at certain intervals. The daily dose to be administered may additionally be dependent on the number of receptors expressed during the course of the disease. It is conceivable that in the initial stage of the disease only a few receptors are expressed on the cell surface and accordingly the daily dose to be administered is lower than in severely ill patients.

The pharmaceuticals according to the invention are prepared by bringing the carbohydrate conjugate into the or a suitable administration form using customary excipients and, if appropriate, additives and/or auxiliaries.

Primary assays for investigation of the action of carbohydrate conjugates of the formulae (I) and (II) on cell adhesion to recombinant, soluble selectin fusion proteins.

Carrying out these assays to measure the inhibitory activity of the compounds according to the invention on cell adhesion of promyelocytic cells by means of selecting is described in detail in European Published Application EP 0 601 417.

Primary assays for investigation of the action of carbohydrate conjugates on cell adhesion to recombinant soluble selectin fusion proteins In order to test the efficacy of the carbohydrate conjugates on the interaction between the E- and P-selectins (former nomenclature ELAM-1 or GMP-140) with their ligands, an assay is used which in each case is specific only for one of these interactions. The ligands are supplied in their natural form as surface structures on promyelocytic HL60 cells. Since HL60 cells contain ligands and adhesion molecules of very different specificity, the desired specificity of the assay can only be produced by means of the binding component. The binding components used were genetically prepared soluble fusion proteins from the in each case extracytoplasmatic domains of E- or P-selectin and the constant region of a human immunoglobulin of the IgG1 subclass.

Preparation of L-selectin-IgG1

For the preparation of soluble L-selectin-IgG1 fusion protein, the genetic construct "ELAM-Rg" published by Walz et al., 1990 was used.

For expression, the plasmid DNA was transfected in COS-7 cells (ATCC) by means of DEAE-dextran (Molecular Biology Methods: see Ausubel, F. M., Brent, R., Kingston, R. E., Moore, D. D., Seidman, J. G., Struhl, K. and Smith, J. A. 1990. Current Protocols in Molecular Biology, John Wiley, New York). Seven days after transfection, the culture supernatant is recovered, freed from cells and cell fragments by centrifugation and transferred to 25 mM HEPES pH 7.0, 0.3 mM PMSF, 0.02% sodium azide and stored at +4° C.

Walz, G., Aruffo, A., Kolanus, W., Bevilacqua, M. and Seed, B. 1990. Recognition by ELAM-1 of the sialyl-Lex determinant on myeloid and tumor cells. Science 250, 1132–1135.

Preparation of P-selectin-IgG1

For preparation of the soluble P-selectin-IgG1 fusion protein, the genetic construct "ICD62Rg" published by Aruffo et al., 1991 is used. The further procedure corresponds to the preparation of L-selectin-IgG1 presented under A1.

Aruffo, A., Kolanus, W., Walz, G., Fredman, P. and Seed, B. 1991. CD62/P-selectin recognition of myeloid and tumor cell sulfatides. Cell 67, 35–44.

Preparation of CD4-IgG1

For the preparation of the soluble CD4-IgG1 fusion protein, the genetic construct "CD4:IgG1 hinge" published by Zettlemeissl et al., 1990 is used. The further procedure corresponds to the preparation of L-selectin-IgG1 presented under A1.

Zettlemeissl, G., Gregersen, J.-P., Duport, J. M., Mehdi, S., Reiner, G. and Seed, B. 1990. Expression and characterization of human CD4: Immunoglobulin Fusion Proteins. DNA and Cell Biology 9, 347–353.

Carrying out HL60 cell adhesion assays on recombinant, soluble adhesion molecules 1. 96-well microtiter test plates (Nunc Maxisorb) are incubated at room temperature for 2 hours with 100 μl of a goat anti-human IgG antibody (Sigma) diluted (1+100) in 50 mM Tris pH 9.5. After removing the antibody solution washing is carried out once with PBS.

2. 150 μl of the blocking buffer are left in the wells at room temperature for 1 hour. The composition of the blocking buffer is: 0.1% gelatin, 1% BSA, 5% calf serum, 0.2 mM PMSF, 0.02% sodium azide. After removing the blocking buffer washing is carried out once with PBS.

3. 100 μl each of cell culture supernatant of appropriately transfected and expressing COS cells are pipetted into the wells. Incubation is carried out at room temperature for 2 hours. After removing the cell culture supernatant washing is carried out once with PBS.

4. 20 μl of binding buffer are added to the wells. The binding buffer has the composition: 50 mM HEPES, pH 7.5; 100 mM NaCl; 1 mg/ml BSA; 2 mM $MgCl_2$; 1 mM $CaCl_2$; 3 mM $MnCl_2$; 0.02% sodium azide; 0.2 mM PMSF. 5 μl of the test substance are pipetted into this, mixed by swirling the plate and incubated at room temperature for 10 minutes.

5. 50 ml of an HL60 cell culture containing 200,000 cells/ml are centrifuged at 350 g for 4 minutes. The pellet is resuspended in 10 ml of RPMI 1640 and the cells are centrifuged again. For labeling the cells, 50 μg of BCECF-AM (Molecular Probes) are dissolved in 5 μl of anhydrous DMSO; 1.5 ml of RPMI 1640 are then added to the BCECF-AM/DMSO solution. The cells are resuspended using this solution and incubated at 37° C. for 30 minutes. After centrifugation at 350 g for 2 minutes, the labeled cell pellet is resuspended in 11 ml of binding buffer and the resuspended cells are distributed into the microtiter plate wells in 100 μl aliquots. The plate is allowed to stand at room temperature for 10 minutes in order to allow the cells to sediment on the bottom of the test plate. In the course of this, the cells have the opportunity to adhere to the coated plastic.

6. To stop the test, the microtiter plate is immersed completely in the stop buffer (25 mM tris, pH 7.5; 125 mM NaCl; 0.1% BSA; 2 mM $MgCl_2$; 1 mM $CaCl_2$; 3 mM $MnCl_2$; 0.02% sodium azide) at an angle of 45°. The stop buffer is removed from the wells by inversion and the procedure is repeated a further two times.

7. Measurement of the BCECF-AM-labeled cells firmly adhering to the wells is carried out in a cytofluorimeter (Millipore) at a sensitivity setting of 4, an excitation wavelength of 485/220 nm and an emission wavelength of 530/250 nm.

The results accordingly obtained for the determination of HL60 cell adhesion to the recombinant, soluble adhesion molecules E-selectin and P-selectin are found in Table 1.

Further suitable assay systems, such as, for example, the investigation of cell adhesion to stimulated, human endothelial cells (HUVEC), to frozen sections of lymphatic tissue and on leucocyte adhesion in the rat in vivo by means of intravital microscopy, are likewise described in detail in the cited publication.

Surprisingly, the compounds obtainable by addition of relatively large lipophilic radicals, amino acids, lipopeptides and peptides to the tetrasaccharides having a sialyl-Lewis X or sialyl-Lewis A structure especially show distinctly improved efficacy (for data see Table 1).

The following examples further illustrate the invention. Percentage data relate to the weight. Mixing ratios in the case of liquids relate to the volume if no other details are given.

EXAMPLE 1

Synthesis of (2,3,4-tri-O-benzyl-α-L-fucopyranosyl)-(1→3)-2-acetamido-1-azido-4,6-O-benzylidene-1,2-dideoxy-β-D-glucopyranose (4) (FIG. 1)

2-Acetamido-1-azido-4,6-O-benzylidene-1,2-dideoxy-β-D-glucopyranose (3) (36.0 g, 108 mmol) and ethyl 2,3,4-tri-O-benzyl-1-thio-β-L-fucopyranoside (2) (67.2 g, 140 mmol) are stirred over molecular sieve (3A) for 1 hour in dichloromethane/DMF (700 ml, 1:1). After addition of tetrabutylammonium bromide (62.7 g, 194 mmol) and copper (II) bromide (38.6 g, 173 mmol), the mixture is stirred at room temperature for 16 hours. It is filtered through silica gel, rinsed with dichloromethane (1.5 l) and washed with saturated sodium hydrogen carbonate solution followed by saturated sodium chloride solution. Removal of the solvents in vacuo and column chromatography on silica gel (i-hexane/ethyl acetate 4:1) yields the disaccharide (4) (68.0 g, 91%).

$[\alpha]_D^{20}$=−143.3° (1/$CH_2Cl_2$); $^1$H-NMR (300 MHz, $CDCl_3$): δ=0.88 (d, 3H, 6-$H_{Fuc}$), 1.61 (s, 3H, NHAc), 5.05 (d, 1H, 1-$H_{Fuc}$), 5.52 (s, 1H, CH-benzylidene), 7.25–7.4 (m, 20H, benzyl).

EXAMPLE 2

Synthesis of (2,3,4-tri-O-benzyl-α-L-fucopyranosyl)-(1→3)-2-acetamido-1-azido-6-O-benzyl-1,2-dideoxy-β-D-glucopyranose (5) (FIG. 1)

Compound (4) (69.0 g, 100 mmol) and sodium cyanoborohydride (63.0 g, 1.0 mol) are stirred at room temperature for 1 hour over molecular sieve (120 g, 4 Å) in tetrahydrofuran (1 l). With checking by means of thin-layer chromatography (TLC), a solution of HCl in ether is cautiously added dropwise until the initially vigorous evolution of gas subsides, a colorless precipitate being deposited. Additional sodium cyanoborohydride and further HCl solution in ether are introduced with careful TLC checking until an almost complete reaction is achieved. The mixture is neutralized with sodium hydrogen carbonate, taken up with dichloromethane, washed with saturated sodium hydrogen carbonate solution, ethanolamine (5% in water) followed by saturated sodium chloride solution. Concentration and column chromatography on silica gel (toluene/ethyl acetate 4:1) yields the disaccharide (5) (53.0 g, 76%) as an amorphous solid.

$[\alpha]_D^{20}$=−83.9° (1/$CH_2Cl_2$); $^1$H-NMR (300 MHz, $CDCl_3$): δ=1.16 (d, 3H, 6-$H_{Fuc}$), 1.58 (s, 3H, NAc), 4.95 (d, 1H, 1-$H_{Fuc}$), 7.1–7.6 (m, 20H, benzyl).

EXAMPLE 3

Synthesis of (6-O-benzyl-β-D-galactopyranosyl)-(1→4)-[(2,3,4-tri-O-benzyl-α-L-fucopyranosyl) (1→3)]-(1→3)-2-acetamido-1-azido-6-O-benzyl-1,2-dideoxy-β-D-glucopyranose (7) (FIG. 1)

A solution of compound (5) (27.0 g, 35.9 mmol) and O-(2,3,4-tri-O-acetyl-6-O-benzyl-α/β-galactopyranosyl) trichloroacetimidate (6) (30.8 g, 53.8 mmol) in 500 ml of dichloromethane is stirred over molecular sieve (4A) for 1 h. TMSOTf (797 mg, 3.6 mmol) is added dropwise to the solution in the course of 3 hours and it is then neutralized with solid sodium hydrogen carbonate. The crude product is treated with dichloromethane (1.5 l) and washed with saturated sodium hydrogen carbonate solution followed by saturated sodium chloride solution. After drying with $MgSO_4$ and concentrating in vacuo, the crude product is dissolved in methanol (1 l) and treated with 10 ml of a 0.1M solution of $NaOCH_3$ in methanol. After stirring at room temperature for 2 hours, the mixture is neutralized with ion exchanger (Amberlite® IR-120) and the solvent removed in vacuo. Subsequent column chromatography (CC) on silica gel (dichloromethane/methanol 40:1) yields compound (7) (16.5 g, 46%) as an amorphous solid.

$[\alpha]_D^{20}$=−88.3 (1/CH$_2$Cl$_2$); $^1$H-NMR (300 MHz, CDCl$_3$): δ=1.14 (d, 3H, 6-H$_{Fuc}$), 1.62 (s, 3H, NHAc), 5.14 (d, 1H, 1-H$_{Fuc}$), 6.12 (d, 1H, NHAc), 7.1–7.5 (m, 25H, benzyl).

EXAMPLE 4

Figure 2:
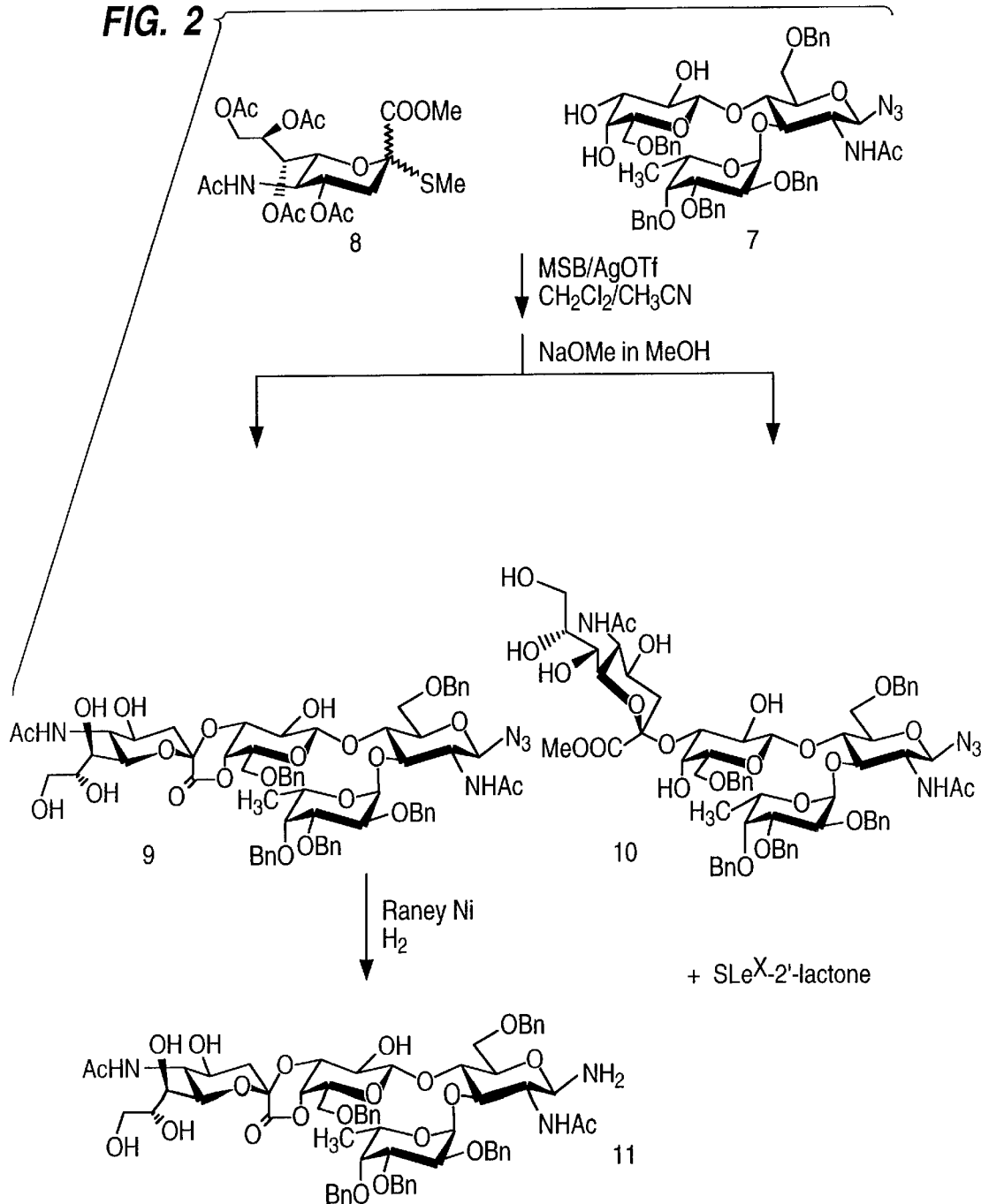
FIG. 2 shows a synthesis of 1-amino-1-deoxy-sialyl-LeX-trisaccharide.

Synthesis of (5-acetamido-3,5-dideoxy-D-glycero-α-D-galacto-2-nonulopyranosyl)-(2→3)-(6-O-benzyl-β-D-galactopyranosyl)-(1→4)-[(2,3, 4-tri-O-benzyl-α-L-fucopyranosyl)-(1→3)]-2-acetamido-1-azido-6-O-benzyl-1,2-dideoxy-β-D-glucopyranose-(1$_{Nana}$→4$_{Gal}$)-lactone (9) (FIG. 2)

A solution of (7) (13.5 g, 13.4 mmol), methyl S-(methyl-5-acetamido-2,4,7,8,9-penta-O-acetyl-3,5-dideoxy-D-glycero-D-galacto- 2-nonulopyranoside) (12.6 g, 24.2 mmol), molecular sieve (3A) and AgOTf (7.93 g, 30.9 mmol) in dichloromethane/acetonitrile (360 ml, 5:1) is treated at −40° C. with methylsulfenyl bromide (MSB, 27 mmol in 31 ml of 1,2-dichloroethane). After stirring at −40° C. for 2 hours, the mixture is neutralized with sodium hydrogen carbonate and filtered.

Dichloromethane (500 ml) is added, and the mixture is washed with saturated sodium hydrogen carbonate solution and then with saturated sodium chloride solution, dried over MgSO$_4$, filtered and concentrated in vacuo. The residue is dissolved in methanol (300 ml) and treated with 1M sodium methoxide solution in methanol and stirred at room temperature for 1 hour. It is neutralized with Amberlite® IR-120 and the solvent is removed in vacuo. Column chromatography on silica gel (dichloromethane/methanol 25:1→10:1) yields the 4'-lactone (9) (7.24 g, 42.2%) and a mixture of methyl ester (10) and lactone (9) (6.0 g).

$[\alpha]_D^{20}$=−77.5° (1/CH$_2$Cl$_2$); $^1$H-NMR (300 MHz, CDCl$_3$): δ=1.05 (d, 3H, 6-H$_{Fuc}$), 1.78 (dd, 1H, 3-H$_{Nana}$), 1.95, 2.0 (2s, 6H, 2 NHAc), 2.48 (dd, 1H, 3-H$_{Nana}$), 4.38 (ddd, 1H, 4-H$_{Nana}$), 5.26, 5.32 (2d, 2H, 1-H$_{Fuc}$, 4-H$_{Gal}$), 7.24–7.5 (m, 25H, benzyl).

EXAMPLE 5

Synthesis of N-(5-acetamido-3,5-dideoxy-D-glycero-α-D-galacto-2-nonulopyranosyl)-(2→3)-(6-O-benzyl-β-D-galactopyranosyl)-(1→4)-[(2,3,4-tri-O-benzyl-α-L-fucopyranosyl)-(1→3)]-2-acetamido-1-amino-6-O-benzyl-1,2-dideoxy-β-D-glucopyranose-(1$_{Nana}$→4$_{Gal}$)-lactone (11) (FIG. 2)

Lactone (9) (300 mg, 0.235 mmol) is dissolved in isopropanol (10% water, 30 ml) and hydrogenated at normal pressure using 300 mg of neutral Raney nickel. After 1 hour, the mixture is filtered and concentrated. The anomeric amine (11) (279 mg, 95%) is obtained in pure form as an amorphous solid and freshly prepared immediately before further reaction thereof (without further characterization).

EXAMPLE 6

Synthesis of the tris-succinimide ester (VII-2)

4-(2-Carboxyethyl)-4-nitroheptanedioic acid (10.0 g, 36.1 mmol), N-ethyl-N'-dimethylaminopropylcarbodiimide hydrochloride (DEC) (31.1 g, 162 mmol) and N-hydroxysuccinimide (18.7 g, 162 mmol) are suspended in 250 ml of dichloromethane and stirred at room temperature for 12 hours. The crystalline colorless product is filtered off, washed twice with 100 ml of dichloromethane each time and dried. Yield C$_{22}$H$_{24}$N$_4$O$_{14}$ (568.4): 17.7 g (86.2%).

$^1$H-NMR (300 MHz, DMSO-d$_6$): δ=2.18 (m, 6H, CH$_2$CH$_2$C=O), 2.74 (m, 6H, CH$_2$CH$_2$C=O), 2.80 (s, 12H, O=CCH$_2$CH$_2$C=O).

EXAMPLE 7

Figures 6, 7:
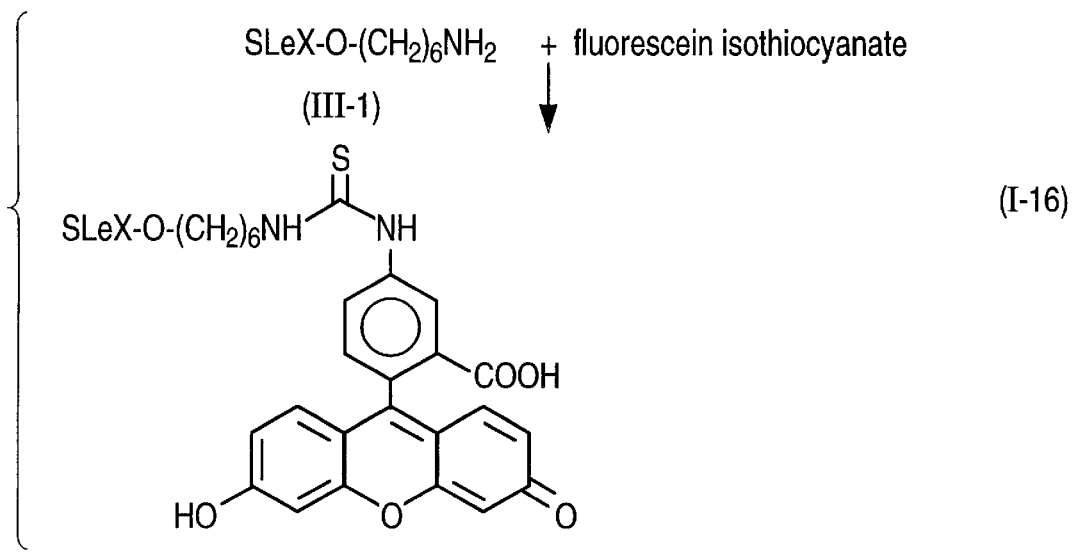
FIG. 6 is a synthesis of (I-16) from SLeX-O-$(CH_2)_2 NH_2$ (III-1) using fluorescein isothiocyanate as an example of the synthesis of a compound SLeX-Y$(CH_2)_n$—[NH(CO)$]_p R^2$ (I, X-type) where Y=O, n=6, p=0 and $R^2$=NH(CS)NH-fluorescein.
FIG. 7 are examples of compounds of formula (II).

Synthesis of tris{2-[N-(5-acetamido-3,5-dideoxy-D-glycero-D-galacto-2-nonulopyranosylate)-(2→3)-(β-D-galactopyranosyl)-(1→4)-[(α-L-fucopyranosyl)-(1→3)]-2-acetamido-1,2-dideoxy-β-D-glucopyranose]amidoethyl}nitro-methane (II-1) (FIG. 7)

Compounds (11) (89 mg, 0.071 mmol) and (VII, Z=OSu, m=q=0) (10 mg, 0.019 mmol) are stirred at room temperature overnight in THF/pyridine (2 ml, 1:1). The solvent is removed in vacuo and, after column chromatography on silica gel (dichloromethane/methanol 10:1), the protected trimeric SLe$^x$ lactone (68 mg) is obtained as an intermediate which is reacted further without further characterization. The compound is dissolved in methanol/dioxane (40 ml, 10:1) and hydrogenated under normal pressure for 2 h after addition of Pd-active carbon (84 mg).

After filtering, concentration, lactone opening with 1M sodium hydroxide solution (0.5 ml) in methanol/water (40 ml/10 ml, 1 h), neutralization with Amberlite® IR-120, removal of the solvents in vacuo and exclusion chromatography on Biogel® P2, compound (II-1) having the empirical formula C$_{103}$H$_{168}$N$_{10}$O$_{71}$ (2682.5) is obtained as a colorless powder. Yield: 40 mg (78.5%).

$[\alpha]_D^{20}$=−25.2 (1/water); $^1$H-NMR (300 MHz, D$_2$O): δ=1.05 (d, 3H, 6-H$_{Fuc}$), 1.66 (dd, 1H, 3-H$_{Nana}$), 1.86, 1.90 (2s, 6H, 2NHAc), 2.64 (dd, 1H, 3-H$_{Nana}$), 4.36 (d, 1H, 1-H$_{Gal}$), 4.951 4.98 (2d, 2H, 1-H$_{Fuc}$, 1-H$_{GlcNAc}$); $^1$C-NMR (75.4 MHz, D$_2$O): δ=177.9, 177.8, 177.0, 176.7 (C=O), 104.5 (1C$_{Gal}$), 102.5 (2-C$_{Nana}$), 101.5 (1-C$_{Fuc}$), 95.7 (C—NO$_2$), 81.1, 79.9, 78.5, 78.2, 77.8, 75.8, 74.9, 74.8, 74.7, 74.5, 72.4, 72.1, 71.1, 71.0, 70.5, 70.2, 69.6, 65.5, 65.4, 64.4, 63.2, 62.4, 57.5, 54.6, 42.7, 33.2, 33.0, 25.1, 24.9, 18.2; ESI (Electrospray ionization): 1364.1 (M+2Na)$^{2+}$.

EXAMPLE 8

Synthesis of benzyloxycarbonyl-Gly-Gly-Gly-N-(5-acetamido-3,5-dideoxy-D-glycero-D-galacto-2-nonulopyranosylate)-(2→3)-(6-O-benzyl-α-L-fucopyranosyl)-(1→3)]-2-acetamido-6-O-benzyl-1, 2-dideoxy-β-D-glucopyranose-(1$_{Nana}$→4$_{Gal}$)lactone (13). (FIG. 3)

Compound (11) (130 mg, 0.104 mmol) and Z-Gly-Gly-Gly-Su (52 mg, 0.124 mmol) are dissolved in DMF/dichloromethane (2 ml, 1:1). After 24 hours, the solvent is removed in vacuo. Column chromatography on silica gel (dichloromethane/methanol 10:1) yields the protected intermediate (13) (98 mg, 60.5%) having the empirical formula C$_{80}$H$_{96}$N$_6$O$_{26}$ (1557.67) as an amorphous solid. $^1$H-NMR (300 MHz, CD$_3$OD): δ=0.99 (d, 3H, 6-H$_{Fuc}$), 1.69 (dd, 1H, 3-H$_{Nana}$), 1.80, 1.89 (2s, 6H, 2NHAc), 2.39 (dd, 1H, 3-H$_{Nana}$), 4.28 (ddd, 1H, 4-H$_{Nana}$), 4.96, 5.22 (2d, 2H, 1-H$_{Fuc}$, 4-H$_{Gal}$).

EXAMPLE 9

Synthesis of Gly-Gly-Gly-N-(5-acetamido-3,5-dideoxy-D-glycero-D-galacto-2-nonulopyranosylate) -(2→3)-(β-D-galactopyranosyl)-( 1→4)-[(α-L-fucopyranosyl)-(1→3)]-2-acetamido-1,2-dideoxy-β-D-glucopyranose-(1$_{Nana}$→4$_{Gal}$)-lactone (14). (FIG. 3)

Compound (13) (90 mg, 0.059 mmol) is dissolved in methanol/dioxane/acetic acid (40 ml, 2:1:1) and, after addition of Pd-active carbon (50 mg), hydrogenated with hydrogen under normal pressure for 16 hours. After filtration the solvents are removed in vacuo. Exclusion chromatography on Biogel®-P2 yields compound (14) having the empirical formula $C_{37}H_{61}N_6O_{24}$ (973.9) as an amorphous solid (49 mg, 86%), which is reacted immediately without further characterization.

EXAMPLE 10

Synthesis of Gly-Gly-Gly-N-(5-acetamido-3,5-dideoxy-D-glycero-D-galacto-2-nonulopyranosylate)-(2→3)-(β-D-galactopyranosyl)-(1→4)-[(α-L-fucopyranosyl)-((1→3)]-2-acetamido-1,2-dideoxy-β-D-glucopyranose (I-1). (FIG. 3)

Compound (14) (45 mg, 0.046 mmol) is dissolved in methanol/water (10 ml, 1:10). A pH of 9 is adjusted using sodium hydroxide solution and the mixture is stirred for 20 minutes. After neutralization with Amberlite® IR-120, filtration, removal of the solvents in vacuo and exclusion chromatography on Biogel® P2, compound (I-1) (43.3 mg, 95%) having the empirical formula $C_{37}H_{62}N_6O_{25}$ (990.9) is obtained as a colorless, amorphous solid.

EXAMPLE 11

Synthesis of the trimethyl ester (VII-3)

4-(2-Carboxyethyl)-4-nitroheptanedioic acid tris-succinimide ester (VII-2) (2.0 g, 3.5 mmol), 50 ml of dry pyridine, methyl 6-aminohexanoate (2.11 g, 14.6 mmol) and 1.5 ml of triethylamine are stirred at 50° C. for 5 hours. The volatile components are distilled off in vacuo and the residue is concentrated a further two times using 50 ml of toluene each time. The crude product is taken up in ethyl acetate and washed with saturated sodium chloride solution and with saturated sodium hydrogen carbonate solution. The product (VII-3) is obtained as a syrup which is reacted further without purification: yield $C_{31}H_{54}N_4O_{11}$ (658.8): 1.95 g (85%). $^1$H-NMR (300 MHz, DMSO-$d_6$): δ=1.10–1.60 (m, 18H, NHCH$_2$CH$_2$CH$_2$CH$_2$CH$_2$C=O), 2.02 (m, 12H, CH$_2$CH$_2$—C=O), 2.30 (t, 6H, CH$_2$COOMe), 3.00 (dt, 6H, CH$_2$NH), 2.57 (s, 9H, Me), 7.85 (t, 3H, NH).

EXAMPLE 12

Synthesis of the tricarboxylic acid (VII-4)

The trimethyl ester (VII-3) (1.95 g, 2.9 mmol) is stirred at room temperature for 72 hours with 10 ml of methanol and 4 ml of 1M NaOH. After acidifying with HCl to pH=2, the product is extracted with diethyl ether and, after drying, obtained as a syrup: yield $C_{28}H_{48}N_4O_{11}$ (616.7): 1.7 g (93%). $^1$H-NMR (300 MHz, DMSO-$d_6$): δ=1.10–1.60 (m, 18H, NHCH$_2$CH$_2$CH$_2$CH$_2$CH$_2$C=O), 2.02 (m, 12H, CH$_2$CH$_2$C=O), 2.19 (t, 6H, CH$_2$CO$_2$H), 3.00 (dt, 6H, CH$_2$NH), 7.85 (t, 3H, NH).

EXAMPLE 13

Synthesis of the tris-succinimide ester (VII-5)

The tricarboxylic acid (VII-4) (235 mg, 0.38 mmol), N-hydroxysuccinimide (218 mg, 1.9 mmol) and dicyclohexylcarbodiimide (DCC, 281 mg, 1.4 mmol) in 10 ml of THF are stirred overnight at room temperature. After separating off the urea, the filtrate is taken up in ethyl acetate and filtered again in the cold. After washing with water, concentrating and drying, the product is obtained as a colorless solid. Yield $C_{40}H_{57}N_7O_{17}$ (907.9): 325 mg (94%). $^1$H-NMR (300 MHz, DMSO-$d_6$): δ=1.15–1.70 (m, 18H, NHCH$_2$CH$_2$CH$_2$CH$_2$), 2.02 (m, 12H, CH$_2$CH$_2$C=O), 2.65 (t, 6H, CH$_2$CO$_2$H), 2.80 (s, 12H, OSu), 3.00 (dt, 6H, CH$_2$NH), 7.86 (t, 3H, NH).

EXAMPLE 14

Synthesis of the protected RGD-Ala-SLeX conjugate

Z-Arg(Z2)-Gly-Asp(-O-benzyl)-Ala-N-(5-acetamido-3,5-dideoxy-D-glycero-D-galacto-2-nonulopyranosylate)-(2→3)-(β-D-galactopyranosyl)-(1→4)-[(α-L-fucopyranosyl)-(1→3)]-2-acetamido-1,2-dideoxy-β-D-glucopyranose-($1_{Nana}$→$4_{Gal}$)-lactone as a precursor of the compound (I-2) (FIG. 4):

Compound (11) (300 mg, 0.24 mmol) and Z-Arg(Z2)-Gly-Asp(OBn)-Ala-OH (270 mg, 0.3 mmol) are dissolved in DMF (4 ml). 1-Hydroxybenzotriazole (41 mg, 0.3 mmol), O-(1H-benzotriazol-1-yl)-N,N,N,N-tetramethyluronium tetrafluoroborate (231 mg, 0.72 mmol) and N-ethyldiisopropylamine (78 mg, 0.6 mmol) are added successively and the mixture is then stirred at room temperature for 1 hour. The crude product is taken up in dichloromethane (300 ml) and washed with water, followed by aqueous sodium hydrogen carbonate solution. After drying with MgSO$_4$, the solvents are removed in vacuo.

Medium pressure chromatography on silica gel (dichloromethane/methanol=13:1) yields the protected RGD-Ala-SLeX conjugate (335 mg, 65%) as an amorphous, white solid. $^1$H-NMR (300 MHz, CD$_3$OD): δ=1.08 (d, 3H, 6-H$_{Fuc}$), 1.3 (d, 3H, b-H$_{Ala}$), 1.78 (dd, 1H, 3-H$_{Nana}$), 1.91, 2.0 (2s, 6H, 2 NHAc), 2.49 (dd, 1H, 3-H$_{Nana}$), 2.79, 3.01 (2dd, 2H, b-H$_{Asp}$), 4.46 (d, 1H, 1-H$_{Gal}$), 5.3 (d, 1H, 1-H$_{Fuc}$).

EXAMPLE 15

Synthesis of Arg-Gly-Asp-N-(5-acetamido-3,5-dideoxy-D-glycero-D-galacto-2-nonulopyranosylate)-(2→3)-(β-D-galactopyranosyl)-(1→4)-[(α-L-fucopyranosyl)-(1→3)]-2-acetamido-1,2-dideoxy-β-D-glucopyranose (I-2) (FIG. 4)

The protected precursor from Example 14 (125 mg, 0.059 mmol) is dissolved in methanol/dioxane/acetic acid (40 ml, 2:1:1) and, after addition of Pd-active carbon (125 mg) hydrogenated with hydrogen under normal pressure for 16 hours. After filtration, the solvents are removed in vacuo. Lactone opening is carried out using 1M sodium hydroxide solution (0.5 ml) in methanol/water (20 ml, 1:10) at pH 8.5. After neutralization with Amberlite® IR-120, filtration, removal of the solvents in vacuo and exclusion chromatography on Biogel® P2, compound (I-2) (84 mg, 58%) of empirical formula $C_{46}H_{78}N_{10}O_{28}$ (1219.31) is obtained as a colorless, amorphous solid. $^1$H-NMR (300 MHz, D$_2$O): δ=1.18 (d, 3H, 6-H$_{Fuc}$), 1.37 (d, 3H, b-H$_{Ala}$), 1.8 (dd, 1H, 3-H$_{Nana}$), 1.99, 2.04 (2s, 6H, 2 NHAc), 2.6–2.9 (3dd, 3H, b-H$_{Asp}$, b-H$_{Asp}$, 3-H$_{Nana}$), 4.52 (d, 1H, 1-H$_{Gal}$), 5.1 (d, H, 1-H$_{Fuc}$); FAB-MS (Fast Atom Bombardment): 1219.5 (MH)+.

EXAMPLE 16

Synthesis of (I-5) having the SLeX configuration (FIG. 4)

The compound is prepared from the SLeX tetrasaccharide (III; n=6) of the formula $C_{37}H_{65}N_3O_{23}$ (919.9), which is obtainable according to the procedure in EP 0 601 417 (18.5 mg, 0.020 mmol), and the commercially available (Bachem) active ester Z-Glu(OBn)ONp (9.9 mg, 0.020 mmol) by stirring in pyridine (15 ml) for 24 hours at room temperature. After TLC checking (BuOH/acetone/HOAc/water 35:35:7:23), the product which is more lipophilic in comparison with the carbohydrate starting material is formed having an $R_f$ value of 0.76 (starting material: $R_f$ 0.21). After concentrating to 1 ml, the product is crystallized by stirring with 30 ml of ethyl acetate and isolated by centrifugation. Crystallization by stirring and centrifugation is repeated a further two times. The crude material (17 mg) is eluted on a Biogel® column (18×170 mm) by means of water and lyophilized. Yield: 16.0 mg (63%) of the compound $C_{57}H_{84}N_4O_{28}$ (1273.3). For further reaction see Example 17.

EXAMPLE 17

Synthesis of (I-6) having the SLeX configuration (FIG. 4)

The compound is prepared from the protected intermediate described above (16.8 mg, 0.013 mmol) by hydrogenation with Pd/active carbon in 8 ml of methanol. Yield of the compound $C_{42}H_{72}N_4O_{26}$ (1049.03). FAB mass spectrum (3-nitrobenzyl alcohol/NaCl): m/e=1049.3 [MH]$^+$, 1073.3 [M+Na]$^+$.

EXAMPLE 18

Synthesis of (I-7) having the SLeX configuration (FIG. 4)

SLeX tetrasaccharide (III; n=6) of the formula $C_{37}H_{65}N_3O_{23}$ (919.9), prepared according to the procedure in EP 0 601 417 (23.9 mg, 0.026 mmol), and succinic anhydride (2.6 mg, 0.026 mmol) in 10 ml of pyridine are reacted at 10° C. for 12 hours (TLC checking). After concentration, the product is lyophilized from water.

Yield of the compound $C_{41}H_{69}N_3O_{26}$ (1019.03): 25.2 mg (92%).

FAB mass spectrum (3-nitrobenzyl alcohol): m/e=1018.4 [M–H]$^-$.

EXAMPLE 19

Synthesis of the SLeX-Ser conjugate (I-8) (FIG. 4)

SLeX tetrasaccharide (III; n=6 in the lactone form $1_{Nana} \rightarrow 4_{Gal}$) of empirical formula $C_{37}H_{63}N_3O_{22}$ (901.9), prepared according to the procedure in EP 0 601 417 (70.0 mg, 0.077 mmol) and Z-Ser(OBn)-OSu (36.0 mg, 0.084 mmol) in 20 ml of pyridine are stirred at room temperature for 20 hours (TLC checking). After concentration, the lactone intermediate is hydrolyzed at pH 12 in 10 ml of methanol using 1N NaOH (TLC checking). After neutralization with acidic ion exchanger, it is concentrated and chromatographed on Sephadex® LH-20 (35×70 mm) using methanol. The compound $C_{55}H_{82}N_4O_{27}$ (1231.3) is obtained in a yield of 78 mg (90.5%) and can be deprotected by catalytic hydrogenation completely analogously to the manner described in Example 16 for the SLeX-Glu conjugate. From 53 mg (0.043 mmol), the free SLeX-Ser conjugate $C_{40}H_{70}N_4O_{25}$ (1007.0) is thus obtained in a yield of 62 mg (80%) based on the SLeX tetrasaccharide (III; n=6 in the lactone form $1_{Nana} \rightarrow 4_{Gal}$).

EXAMPLE 20

Figure 5:
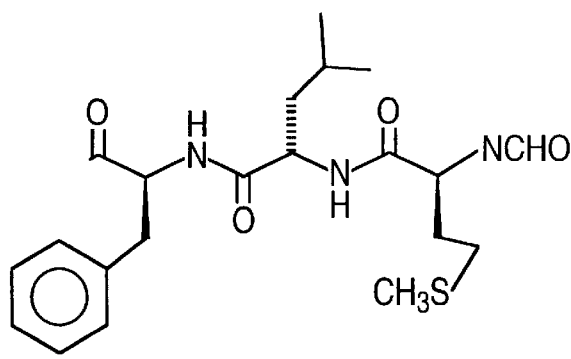
FIG. 5 are examples of compounds SLeX/A-Y$(CH_2)_n$[NH(CO)$]_p R^2$ (I).
Figure 5:
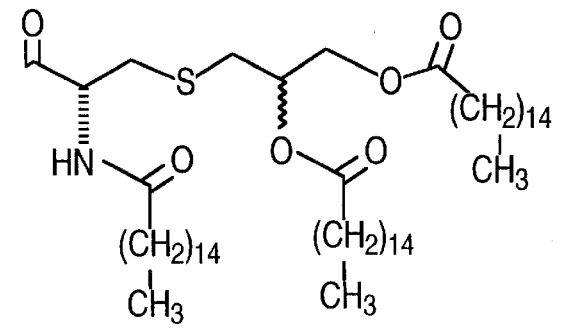
Figure 5:
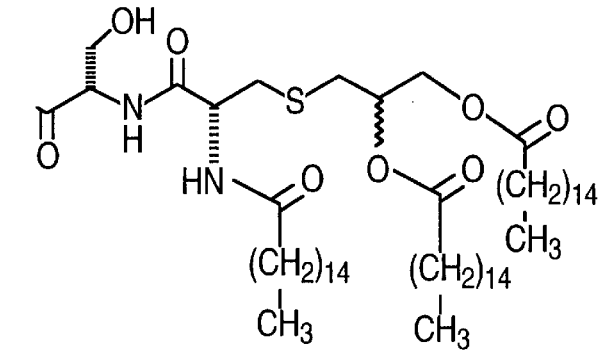
Figure 5:
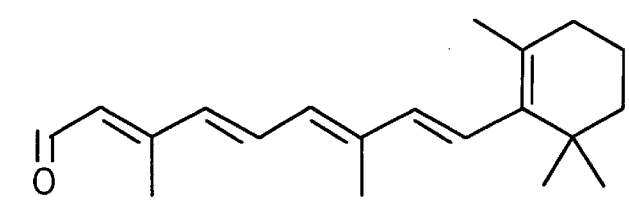

Synthesis of the Pam$_3$Cys-Ser-SLeX conjugate (I-14) (see FIG. 5)

The SLeX-Ser conjugate (I-8) prepared according to Example 19 of empirical formula $C_{40}H_{70}N_4O_{25}$ (20 mg, 0.02 mmol) is reacted in 5 ml of pyridine for 24 hours at room temperature with Pam$_3$Cys-OSu (30.2 mg, 0.03 mmol; prepared according to Int. J. Peptide Protein Res. 37, 1991, 46). After concentration, the residue is chromatographed on Toyopearl® HW-40 using the eluent methanol/dichloromethane (1:1). The Pam$_3$Cys-Ser-SLeX conjugate (I-14) of empirical formula $C_{94}H_{171}N_5O_{31}S$ (1899.4) is obtained. Yield: 25 mg (66%). FAB-MS (glycerol, KCl): m/e=1897.1.

The derivative of this compound provided with a benzyl protective group on the serine is obtained completely analogously by terminating the hydrogenation of the Z- and benzyl-protected precursor from Example 19 after selective removal of the Z protective group (TLC checking) and reacting the intermediate with Pam$_3$Cys-OSu analogously to the manner described above. The benzyl derivative of (I-14) having the empirical formula $C_{101}H_{177}N_5O_{31}S$ (1989.6) is obtained.

FAB-MS (glycerol, KCl): m/e=1988.1. $^1$H-NMR (500 MHz, CD$_3$OD/CDCl$_3$=2/1): δ=0.90 (3t, 9H, CH$_3$-Pam), 1.17 (d, 3H, 6-H$_{Fuc}$), 1.20–1.70 (m, ca. 86H, CH$_2$), 1.74 (m, 1H, 3-H$_{Nana/ax}$), 1.96, 2.03 (2s, 6H, 2NAc), 2.20–2.40 (m, 6H, C$_{14}$H$_{29}$CH$_2$COO), 2.68–2.91 (m, 3H, 1×CH$_3$S and 3-H$_{Nana/eq}$), 3.33 (m, 2H, CH$_2$CH$_2$NHCO), 5.04 (d, 1H, 1-H$_{Fuc}$), 5.18 (m, 1H, C$_{14}$H$_{29}$CH$_2$CO—OCH), 7.30 (m, 5H, Phe). $^{13}$C-NMR (125.7 MHz, CD$_3$OD/CDCl$_3$=2/1): δ=103.42, 101.82, 100.23, 99.41 (1-C$_{Gal}$, 1-C$_{GlcNAc}$, 2-C$_{Nana}$, 1-C$_{Fuc}$), 16.31(6-C$_{Fuc}$), 14.37 (16-C-Pam, 3×).

EXAMPLE 21

Synthesis of the conjugate (I-9) having the SLeX configuration (FIG. 4)

SLeX tetrasaccharide (III; n=6) of the formula $C_{37}H_{65}N_3O_{23}$ (919.9), prepared according to the procedure in EP 0 601 417 (20.0 mg, 0.022 mmol) is dissolved in 10 ml of pyridine and treated with 7.3 mg (0.022 mmol) of succinimidyl 4-(N-maleimidomethyl)cyclohexane-1-carboxylate (SMCC, Pierce). After stirring at room temperature for 20 hours (TLC checking), the product is precipitated with ethyl acetate and isolated by centrifugation. After washing with ethyl acetate, the product is dissolved in water, sterile-filtered and lyophilized. 20.3 mg (81%) of the compound (I-9) having the empirical formula $C_{49}H_{78}N_4O_{26}$ (1139.17) are obtained.

FAB-MS (3-nitrobenzyl alcohol): m/e=1137.5 [M–H]$^-$.

If the SLeX tetrasaccharide (III; n=6 in the lactone form $1_{Nana} \rightarrow 4_{Gal}$) of the empirical formula $C_{37}H_{63}N_3O_{22}$ (901.9), prepared according to the procedure in EP 0 601 417, is analogously reacted with SMCC in pyridine and the lactone is cleaved with NaOH in methanol/water analogously to the manner described in Example 19, the maleimide ring is opened and, after acidification and purification of the product by means of chromatography on Biogel®, the hydrolysis product of empirical formula $C_{49}H_{80}N_4O_{27}$ (1157.17) is thus obtained. FAB-MS (glycerol, KCl): m/e=1155.6 [M–H]$^-$. MS with electrospray ionization (ESI, glycerol matrix): m/e=1158 [M–H]$^+$; m/e=1180 [M+Na]$^+$.

The compound slowly hydrolyzes further in aqueous solution with elimination of maleic acid and $C_{45}H_{78}N_4O_{24}$ (1059.12) is formed. FAB-MG (glycerol): m/e=1057.6 [M–H]$^-$.

EXAMPLE 22

Synthesis of the conjugate (I-10) having the SLeX configuration (FIG. 4)

SLeX tetrasaccharide (III; n=6) of the formula $C_{37}H_{65}N_3O_{23}$ (919.9), prepared according to EP 0 601 417

(21.3 mg, 0.023 mmol), is dissolved in 10 ml of pyridine and treated with 7.24 mg (0.023 mmol) of N-succinimidyl 3-(2-pyridyldithio)propionate (SPDP, Pierce). After stirring at room temperature for 16 hours (TLC checking), the product is precipitated using ethyl acetate and isolated by centrifugation. After washing with ethyl acetate, the product is dissolved in water, sterile-filtered and lyophilized. 20.2 mg (78%) of the compound (I-10) having the empirical formula $C_{45}H_{72}N_4O_{24}S_2$ (1117.2) are obtained.

FAB-MS (3-nitrobenzyl alcohol): m/e=1115.5 [M−H]⁻.

EXAMPLE 23

Synthesis of the conjugate (I-11) having the SLeX configuration (FIG. 4)

SLeX tetrasaccharide (III; n=6) of the formula $C_{37}H_{65}N_3O_{23}$ (919.9), prepared according to the procedure in EP 0 601 417 (22.0 mg, 0.024 mmol), is dissolved in 10 ml of pyridine and treated with 8.2 mg (0.024 mmol) of NHS-biotin (Pierce). After stirring at room temperature for 48 hours (TLC checking), the solvent is removed in vacuo and the product is purified on Biogel®. 23 mg (83%) of the compound (I-11) having the empirical formula $C_{47}H_{79}N_5O_{25}S$ (1146.22) are obtained. FAB-MS (3-nitrobenzyl alcohol): m/e=1144.4 [M−H]⁻.

The streptavidin conjugate of this compound is obtained as follows: Streptavidin (10 mg of Pierce No. 21125) is dissolved in 5 ml of water and treated with 1.54 mg (1.34 μmol) of (I-11). After 1 hour, the product is purified on Biogel® P2. After lyophilization, 13.7 mg of colorless SLeX-biotin-streptavidin conjugate are obtained.

EXAMPLE 24

Synthesis of the conjugate (I-12) having the SLeX configuration (FIG. 5)

N-Formyl-Met-Leu-Phe-OH (100 mg, 0.23 mmol), N-hydroxy-succinimide (29 mg, 0.25 mmol) and dicyclohexylcarbodiimide (52 mg, 0.25 mmol) are stirred in 3 ml of DMF for 12 hours. After concentration in vacuo, the residue is taken up in 5 ml of pyridine and treated with SLeX tetrasaccharide (III; n=6 in the lactone form $1_{Nana} \rightarrow 4_{Gal}$) of empirical formula $C_{37}H_{63}N_3O_{22}$ (901.9), prepared according to the procedure in EP 0 601 417 (90 mg, 0.099 mmol), and with diisopropylethylamine (0.5 ml).

After stirring at room temperature for 14 hours, the pyridine is removed in vacuo. The residue is dissolved in 5 ml of methanol and 1 ml of water and adjusted to pH=11.5 using 1N NaOH. After 1 hour, the mixture is neutralized with 0.1N HCl and the product is purified on Toyopearl® HW-40/methanol. 56 mg (42%) of the product (I-12) having the empirical formula $C_{58}H_{94}N_6O_{27}S$ (1339.46) are obtained.

MS with electrospray ionization (ESI, glycerol matrix): m/e=1361.6 [M+Na]⁺. ¹H-NMR (500 MHz, CD₃OD): δ=0.85, 0.91 (2d, 6H, CH₃-Leu), 1.16 (d, 3H, 6-$H_{Fuc}$), 1.73 (m, 1H, 3-$H_{Nana}$), 1.95, 2.00 (2s, 6H, 2 NAc), 2.08 (s, 3H, CH₃S), 2.50 (m, CH₂S), 2.87 (m, 1H, 3-$H_{Nana}$), 3.29 (m, 2H, CH₂CH₂NHCO), 4.04 (m, 1H, 3-$H_{Gal}$), 5.05 (d, 1H, 1-$H_{Fuc}$), 7.22 (m, 5H, Phe), 8.10 (s, 1H, NHCHO).

EXAMPLE 25

Synthesis of the Pam₃Cys-SLeX conjugate (I-13) (FIG. 5)

SLeX tetrasaccharide (III; n=6) of the formula $C_{37}H_{65}N_3O_{23}$ (919.9), prepared according to the procedure in EP 0 601 417 (38 mg, 0.041 mmol), is reacted at room temperature for 24 hours with Pam₃Cys-OSu (60.4 mg, 0.06 mmol; Int. J. Peptide Protein Res. 37, 1991, 46) in 10 ml of pyridine. After concentration, the product is purified on Toyopearl® HW-40 using dichloromethane/methanol (1:1). The Pam₃Cys-SLeX conjugate (I-13) of empirical formula $C_{91}H_{166}N_4O_{29}S$ (1812.39) is obtained.

Yield: 40 mg (54%). FAB-MS (glycerol): m/e=1812.4 [MH]⁺.

EXAMPLE 26

Synthesis of Pam₃-Cys-Ala-Gly-SLeX (II-17)

From 50 mg (0.048 mmol) of Pam₃Cys-Ala-Gly-OH (Int. J. Peptide Protein Res. 37, 1991, 46), the OSu ester is prepared analogously to the manner described in Example 24 and reacted at 65° C. in 5 ml of pyridine with 30 mg (0.033 mol) of SLeX tetrasaccharide (III; n=6) of the formula $C_{37}H_{65}N_3O_{23}$ (919.9), prepared according to the procedure in EP 0 601 417, for 30 minutes. After concentration, the product is chromatographed on Toyopearl® HW-40 using the eluent methanol/dichloromethane (1:1). The compound (I-17) of empirical formula $C_{96}H_{174}N_6O_{31}S$ (1940.5) is obtained. Yield: 37 mg (58%).

FAB-MS (glycerol): m/e=1938.1 [M−H]⁻.

EXAMPLE 27

Synthesis of the vitamin A conjugate having the SLeX configuration (I-15) (FIG. 5)

Vitamin A acid (79.5 mg, 0.265 mmol) is reacted for 12 hours with HOSu (33.5 mg, 0.292 mmol) and DCC (57 mg, 0.278 mmol) in 5 ml of dichloromethane and 1 ml of THF (TLC checking). The filtrate is concentrated and dried. Yield of crude product OSu ester: 117 mg. This crude product (24 mg, 0.06 mmol) is reacted at room temperature for 16 hours and then at 40° C. for 8 hours with 54 mg (0.057 mmol) of SLeX tetrasaccharide (III; n=6 in the lactone form $1_{Nana} \rightarrow 4_{Gal}$) of empirical formula $C_{37}H_{63}N_3O_{22}$ (901.9), prepared according to the procedure in EP 0 601 417, and diisopropylethylamine (0.5 ml) under argon in 5 ml of pyridine. After concentration of the solution, the product is crystallized from dichloromethane by stirring and filtered off. The solid is dissolved in 3 ml of water and adjusted to pH=11.5 using 0.1N NaOH. After stirring for 2 hours, the mixture is neutralized and the product is purified by preparative HPLC on Eurosil Bioselect®-100 RP-18 (250×20 mm) using 20 to 60% acetonitrile/water. 29 mg (42%) of (I-15) having the empirical formula $C_{57}H_{91}N_3O_{24}$ (1202.4) are obtained. MS electrospray ionization (ESI, glycerol matrix): m/e=1203 [MH]⁺; as secondary components oxidized species can be detected: m/e=1219, 1235. ¹H-NMR (300 MHz, CD₃OD): δ=1.02 (s, 6H, 2CH₃), 1.15 (d, 3H, 6-$H_{Fuc}$), 1.72 (s, 3H, CH₃), 1.95, 2.00 (2s, 6H, 2NAc), 1.98 (s, 3H, CH₃), 2.29 (s, 3H, CH₃), 2.87 (dd, 1H, 3-$H_{Nana/eq}$), 3.20 (m, 2H, CH₂CH₂NHCO), 4.41, 4.51 (2d, each 1H, 1-$H_{Gal}$, 1-$H_{GlcNAc}$), 5.05 (d, 1H, 1-$H_{Fuc}$), 6.05–6.40 (m, ca. 5H, CH═), 6.05 (dd, J=11 Hz, J=15 Hz, 1H, CH═).

EXAMPLE 28

Synthesis of the fluorescein conjugate (I-16) (FIG. 6)

1.30 g (1.44 mmol) of SLeX tetrasaccharide (III; n=6 in the lactone form $1_{Nana} \rightarrow 4_{Gal}$: $C_{37}H_{63}N_3O_{22}$=901.9), prepared according to the procedure in EP 0 601 417, and 0.57 g (1.46 mmol) of fluorescein isothiocyanate (Fluka No. 46951) in 180 ml of pyridine are stirred at room temperature for 20 hours. After concentrating to dryness, the residue is dissolved in 3 ml of water, adjusted to pH=12 using 0.1N NaOH and after stirring for 1 hour at room temperature neutralized with HCl/water. The product is purified on Biogel® P2 Yield: 1.67 g (88.6%) of solid (orange).

Empirical formula $C_{58}H_{76}N_4O_{28}S$ (1309.3). FAB-MS (glycerol/MeOH): m/e=1309.0 $[MH]^+$, 1330.8 $[M+Na]^+$.

EXAMPLE 29

Synthesis of the trivalent compound (II-2) (FIG. 7)

30 mg (0.033 mmol) of SLeX tetrasaccharide (III; n=6 in the lactone form $1_{Nana} \rightarrow 4_{Gal}$: $C_{37}H_{63}N_3O_{22}$=901.9), prepared according to the procedure in EP 0 601 417, and 5.4 mg (0.01 mmol) of tris-succinimide (VII-2), prepared according to Example 6, are stirred at 60° C. for 7 hours in 7 ml of pyridine. After concentrating, the residue is dissolved in 3 ml of water, adjusted to pH=12 using 1N NaOH, neutralized after 1 hour using acidic ion exchanger and the product is purified on Biogel® P4/water. 24 mg (84%) of the compound (II-2) having the empirical formula $C_{121}H_{204}N_{10}O_{74}$ (2983.0) are obtained as a colorless powder. MS electrospray ionization (ESI): m/e=993.3 $[M-3H]^{3-}$, 1490.4 $[M-2H]^{2-}$.

$^1$H-NMR (500 MHz, $D_2O$): d=1.17 (d, 3H, J=6.5 Hz, 6-$H_{Fuc}$), 1.28–1.38 (m, 4H, $NCH_2CH_2$—$CH_2CH_2CH_2CH_2O$), 1.45–1.59 (m, 4H, $NCH_2CH_2CH_2CH_2CH_2CH_2O$), 1.80 (pseudo-t, J=12 Hz, 1H, 3-$H_{Nana/ax}$), 2.02, 2.04 (2s, 6H, 2NAc), 2.20–2.30 (m, 4H, $CH_2CH_2CNO_2$), 2.77 (dd, 1H, J=4.5 Hz, J=12.5 Hz, 3-$H_{Nana/eq}$) 3.16 (t, 2H, J=6.5 Hz, $CH_2CH_2NHCO$), 3.53 (dd, 1H, J=7.5 Hz, J=9.5 Hz, 2-$H_{Gal}$), 4.09 (dd, 1H, J=3.0 Hz, J=9.5 Hz, 3-$H_{Gal}$), 4.53 (2d, 2H, 1-$H_{Gal}$, 1-$H_{GlcNAc}$), 4.83 (m, 1H, H-5$_{Fuc}$), 5.11 (d, 1H, J=4.0 Hz, 1-$H_{Fuc}$).

$^{13}$C-NMR (125.7 MHz, $D_2O$): δ=175.06, 174.14, 174.12, 173.93 (C=O), 101.66 (1-$C_{Gal}$), 101.01 (1-$C_{GlcNAc}$), 99.70 (2-$C_{Nana}$), 98.65 (1-$C_{Fuc}$), 75.68, 75.29, 74.92, 74.89 (3-$C_{Gal}$, 5-$C_{GlcNAc}$, 3-$C_{GlcNAc}$, 5-$C_{Gal}$), 73.39, 72.94 (4-$C_{GlcNAc}$, 6-$C_{Nana}$), 71.94, 71.88 (4-$C_{Fuc}$, 8-$C_{Nana}$), 70.52 (spacer-$CH_2O$), 69.30, 69.22 (2-$C_{Gal}$, 3-$C_{Fuc}$), 68.36, 68.14 (4-$C_{Nana}$, 7-$C_{Nana}$), 67.75, 67.34, 66.71 (2-$C_{Fuc}$, 4-$C_{Gal}$, 5-$C_{Fuc}$), 62.62 (9-$C_{Nana}$), 61.51 (6-$C_{Gal}$), 59.70 (6-$C_{GlcNAc}$), 55.17 (2-$C_{GlcNAc}$), 51.73 (5-$C_{Nana}$), 39.81, 39.46 (spacer-$CH_2NH$, 3-$C_{Nana}$), 30.64, 30.18 [$C(NO_2)CH_2CH_2$], 28.55, 28.25, 25.75, 24.78 ($NCH_2CH_2CH_2CH_2CH_2O$), 22.31, 22.07 (NAc), 15.31 (6-$C_{Fuc}$).

EXAMPLE 30

Synthesis of the trivalent compound (II-3) (FIG. 7)

98 mg (0.108 mmol) of SLeX tetrasaccharide (III; n=6 in the lactone form $1_{Nana} \rightarrow 4_{Gal}$:$C_{37}H_{63}N_3O_{22}$=901.9), prepared according to the procedure in EP 0 601 417, and 30 mg (0.033 mmol) of tris-succinimide (VII-5), prepared according to Example 13, are stirred at 60° C. for 10 hours in 10 ml of pyridine. After concentrating, the residue is dissolved in 10 ml of water (cloudy solution), adjusted to pH=12 using 1N NaOH, neutralized after 1 hour with acidic ion exchanger and the product is purified on Biogel® P4/water. 17 mg (15% based on VII-5 and 14% based on the tetrasaccharide) of the compound (II-2) having the empirical formula $C_{139}H_{237}N_{13}O_{77}$ (3322.4) are obtained as a colorless powder. MS electrospray ionization (ESI): m/e=1106.5 $[M-3H]^{3-}$; the bivalent compound having the mean molecular weight 2420 is found in the MS only in traces: m/e=805.8 $[M-3H]^{3-}$.

$^1$H-NMR (500 MHz, $D_2O$): δ=1.13 (d, 3H, J=6.5 Hz, 6-$H_{Fuc}$), 1.22–1.33 (m, 6H, $NCH_2CH_2$—$CH_2CH_2CH_2CH_2O$ and $NHCOCH_2CH_2CH_2CH_2CH_2CO$), 1.40–1.60 (m, 8H, $NCH_2CH_2CH_2CH_2CH_2CH_2O$ and $NHCOCH_2CH_2CH_2CH_2CH_2CO$), 1.75 (pseudo-t, J=12 Hz, 1H, 3-$H_{Nana/ax}$), 1.97, 1.99 (2s, 6H, 2NAc), 2.15–2.27 (m, 6H, $CH_2CH_2CNO_2$ and $CH_2CH_2CH_2CONH$), 2.74 (dd, 1H, J=4.5 Hz, J=12.5 Hz, 3-$H_{Nana/eq}$), 3.13 (2t, 4H, J=6.5 Hz, 2×$CH_2NHCO$), 4.04 (dd, 1H, J=3.0 Hz, J=9.5 Hz, 3-$H_{Gal}$), 4.48 (2d, 2H, 1-$H_{Gal}$, 1-$H_{GlcNAc}$), 4.78 (m, 1H, H-5$_{Fuc}$), 5.07 (d, 1H, J=4.0 Hz, 1-$H_{Fuc}$). $^{13}$C-NMR (125.7 MHz, $D_2O$): δ=176.50, 174.92, 173.97, 173.90, 173.79 (CO), 101.52 (1-$C_{Gal}$), 100.88 (1-$C_{GlcNAc}$), 99.56 (2-$C_{Nana}$), 98.51 (1-$C_{Fuc}$), 93.39 ($CNO_2$), 75.55, 75.16, 74.79, 74.76 (3-$C_{Gal}$, 5-$C_{GlcNAc}$, 3-$C_{GlcNAc}$, 5-$C_{Gal}$), 73.25, 72.81 (4-$C_{GlcNAc}$, 6-$C_{Nana}$), 71.95, 71.80 (4-$C_{Fuc}$, 8-$C_{Nana}$), 70.36 (spacer-$CH_2O$), 69.42, 69.17, 68.21, 68.01, 67.62, 67.21, 66.58, (2-$C_{Gal}$, 3-$C_{Fuc}$,4-$C_{Nana}$, 7-$C_{Nana}$, 2-$C_{Fuc}$, 4-$C_{Gal}$, 5-$C_{Fuc}$), 62.49 (9-$C_{Nana}$), 61.38, 59. 56, (6-$C_{Gal}$, 6-$C_{GlcNAc}$), 55.75 (2-$C_{GlcNAc}$), 51.60 (5-$C_{Nana}$), 39.67, 39.17, 39.12 (2×spacer-$CH_2NH$, 3-$C_{Nana}$), 35.58 ($OC_6H_{12}NH$—$COCH_2$), 30.55, and $NHCOCH_2CH_2CH_2CH_2CH_2CO$), 22.17, 21.93 (Nac), 30.06 [$C(NO_2)CH_2CH_2$], 28.45, 28.26, 27.79, 25.64, 25.40, 24.99, 24.68, ($NCH_2CH_2CH_2CH_2CH_2O$ 15.18 (6-$C_{Fuc}$).

EXAMPLE 31

Leucocyte adhesion—testing of the activity in vivo

In inflammatory processes and other conditions activating cytokines, tissue destruction by leucocytes migrating in or blocking the microcirculation plays a crucial role. The first phase, which is crucial for the further disease process, is the activation of leucocytes within the blood stream, in particular in the pre- and postcapillary region. After the leucocytes have left the axial flow of the blood, a first attachment of the leucocytes to the vascular inner wall, i.e. to the vascular endothelium, occurs in this case. All leucocyte effects following thereon, i.e. the active migration through the vascular wall and the subsequent orientated migration in the tissue, are subsequent reactions (Harlan, J. M., Leucocyte-endothelial interaction, Blood 65, 513–525, 1985).

This receptor-mediated interaction of leucocytes and endothelial cells is regarded as an initial sign of the inflammatory process. In addition to the adhesion molecules already physiologically expressed, under the action of inflammatory mediators (leucotrienes, PAF) and cytokines (TNF-alpha, interleukins), a temporally graded, massive expression of adhesion molecules on the cells occurs. They are at present divided into three groups: 1. Immunoglobulin gene superfamily, 2. integrins and 3. selecting. While adhesion takes place between molecules of the Ig gene superfamily and the protein-protein bonds, in the cooperation between selecting lectin-carbohydrate bonds are predominant (Springer, T. A., Adhesion receptors of the immune system. Nature 346, 425–434, 1990; Huges, G., Cell adhesion molecules—the key to a universal panacea, Scrips Magazine 6, 30–33, 1993; Springer, T. A., Traffic signals for lymphocyte recirculation and leucocyte emigration; The multistep paradigm. Cell 76, 301–314, 1994).

Method

The induced adhesion of leucocytes is quantified in the mesenterium of the rat using an intravital microscopic investigation technique (Atherton A. and Born G. V. R., Quantitative investigations of the adhesiveness of circulating polymorphnuclear leucocytes to blood vessel walls. J. Physiol. 222, 447–474, 1972; Seiffge, D. Methoden zur Untersuchung der Rezeptor-vermittelten Interaktion zwischen Leukozyten und Endothelzellen im Entzündungsgeschehen [Methods for the investigation of the receptor-mediated interaction between leucocytes and endothelial cells in inflammatory phenomena] in Ersatz- und Ergänzungsmethoden zu Tierversuchen in der biomedizinischen Forschung [Substitution and replacement methods for animal experiments in biomedical research], Schöffl, H. et al., (Editors) Springer, 1995 (in press)). Lasting anesthesia is initiated under inhalation ether anesthesia by intramuscular injection of urethane (1.25 mg/kg of body weight). After exposing vessels (femoral vein for the injection of substances and carotid artery for blood pressure measurement), catheters are tied into them. After this, the corresponding transparent tissue (mesenterium) is freed according to the standard methods known in the literature and arranged on the microscope stage and coated with warm liquid paraffin at 37° C. (Menger, M. D. and Lehr, H., A. Scope and perspectives of intravital microscopy-bridge over from in vitro to in vivo, Immunology Today 14, 519–522, 1993). The administration of the test substance to the animal is carried out i.v. (10 mg/kg). The experimental increase in blood cell adhesion is induced by cytokine activation by means of systemic administration of lipopolysaccharide (LPS, 15 mg/kg) 15 minutes after administration of test substance (Foster S. J., Mc Cormick L. M., Ntolosi B. A. and Campbell D., Production of TNF-alpha by LPS-stimulated murine, rat and human blood and its pharmacological modulation, Agents and Actions 38, C77–C79, 1993, 18.01.1995). The increased adhesion of leucocytes to the endothelium caused by this means is quantified by direct vital microscopy or with the aid of fluorescent dyes. All measuring operations are recorded by video camera and stored on a video recorder. Over a period of 60 minutes, the number of rolling leucocytes (i.e. all visible rolling leucocytes which are slower than the flowing erythrocytes) and the number of leucocytes adhering to the endothelium (residence period longer than 5 seconds) is determined every 10 minutes. After completion of the experiment, the anesthetized animals are painlessly put to sleep without excitation by systemic injection of T61. For analysis, the results of 8 treated animals in each case are compared with 8 untreated animals (control group) (data in percentages).

The results for the compounds II-2, II-1, I-2, I-9 and for derivatives of I-9 and I-14 are shown in FIG. 8.

TABLE 1

Inhibition of HL60 cell adhesion to soluble, recombinant adhesion molecules.

| Compound | $IC_{50}$ E-Selectin (mM) | $IC_{50}$ P-Selectin (mM) |
|---|---|---|
| I-2 | >0.80 | 0.01 |
| I-6 | 1.20 | n.d. |
| I-7 | 1.15 | 1.50 |
| I-9 | 0.28 | 0.33 |
| I-10 | 0.39 | 0.40 |
| I-11 | 0.59 | 0.60 |
| I-12 | >0.80 | >0.80 |
| I-13 | 0.02 | 0.10 |

TABLE 1-continued

Inhibition of HL60 cell adhesion to soluble, recombinant adhesion molecules.

| Compound | $IC_{50}$ E-Selectin (mM) | $IC_{50}$ P-Selectin (mM) |
|---|---|---|
| I-16 | 0.65 | 0.90 |
| II-1 | 0.38 | >0.80 |
| II-2 | 0.13 | 0.14 |
| II-3 | 0.40 | >1.0 |
| III (n = 6) | 1.0 | 2.0 |

What is claimed is:

1. A compound having the formula I, $$Z-Y-(CH_2)_n-[NH(CO)]_p-R^2 \qquad (I)$$

in which

Z is a branched tetrasaccharide,

Y is oxygen or NH(CO) and $R^2$ is an amino acid or oligopeptide radical of up to 6 amino acids, a lipophilic radical formed from aliphatic or cycloaliphatic units, a combination of aliphatic and heterocyclic units or a triphenylmethane dye, where for Y=oxygen p is 1 and n is an integer from 2 to 10, and for Y=NH(CO) and p=0 n is an integer from 0 to 10, and for Y=NH(CO) and p=1, n is an integer from 1 to 10, and wherein said compound binds to a selection receptor.

2. The compound as claimed in claim 1, wherein $R^2$ has the Formula (II),

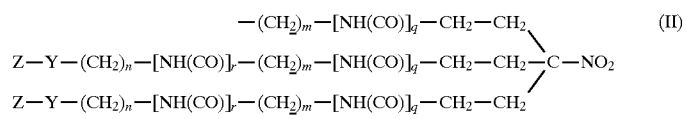

wherein m is an integer from 0 to 10 and r and q can be 0 or 1, provided that when m is 0, either r or q is equal to 0.

3. The compound as claimed in claim 1, wherein $R^2$ is —CH$_2$NH(CO)CH$_2$NH$_2$.

4. The compound as claimed in claim 1, wherein $R^2$ is —CH[(S)—CH$_3$]NHCOCH[(S)—CH$_2$CO$_2$H]NHCO—CH$_2$NHCOCH[(S)—(CH$_2$)$_3$NH(C=NH)NH$_2$]NH$_2$.

5. The compound as claimed in claim 1, wherein $R^2$ is —(CH$_2$)$_6$—NH$_2$.

6. The compound as claimed in claim 1, wherein $R^2$ is —CH(NH$_2$)—(CH$_2$)$_2$—COOH.

7. The compound as claimed in claim 1, wherein $R^2$ is —(CH$_2$)$_2$—COOH.

8. The compound as claimed in claim 1, wherein $R^2$ is —CH(NHCbz)CH$_2$OBn, where Cbz is benzyloxycarbonyl and Bn is benzyl.

9. The compound as claimed in claim 1, wherein

Y is oxygen, n is 6, p is 1 and

R² is

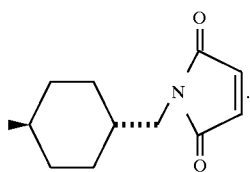

10. The compound as claimed in claim 1, wherein

Y is oxygen, n is 6, p is 1 and

R² is

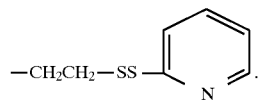

11. The compound as claimed in claim 1, wherein

Y is oxygen, n is 6, p is 1 and

R² is

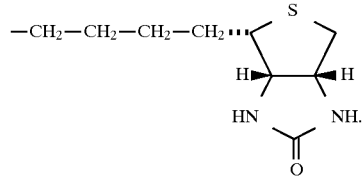

12. The compound as claimed in claim 1, wherein

Y is oxygen, n is 6, p is 1 and

R² is

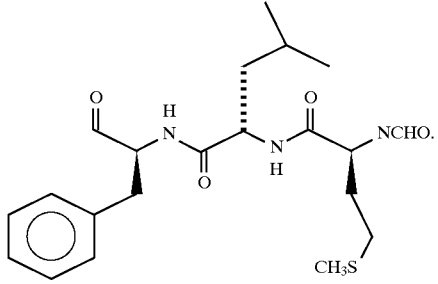

13. The compound as claimed in claim 1, wherein

Y is oxygen, n is 6, p is 1 and

R² is

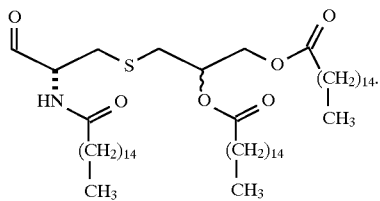

14. The compound as claimed in claim 1, wherein

Y is oxygen, n is 6, p is 1 and

R² is

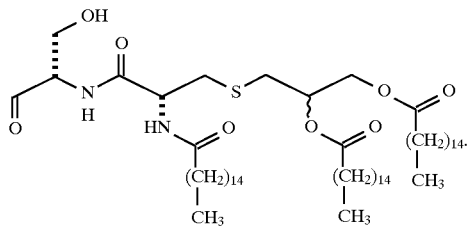

15. The compound as claimed in claim 1, wherein

Y is oxygen, n is 6, p is 1 and

R² is

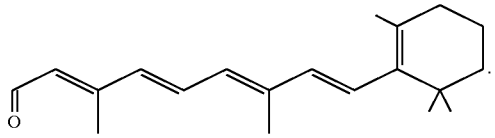

16. The compound as claimed in claim 1, wherein

Y is oxygen, n is 6, p is 1 and

R² is

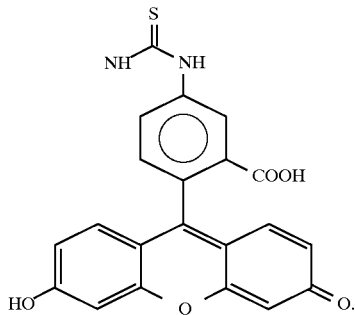

17. The compound as claimed in claim 1, wherein Z is sialyl-Lewis X.

18. The compound as claimed in claim 1, wherein Z is sialyl-Lewis A.

19. A process for the preparation of a compound as claimed in claim 1, which comprises reacting a compound selected from the group consisting of a compound having the formula III, (III) Z—O—(CH$_2$)$_n$—NH$_2$ a compound having formula IV, (IV) Z—NH$_2$ and a compound having formula V, (V) Z—NH(CO)—(CH$_2$)$_n$—NH$_2$ in which Z is a branched tetrasaccharide and n is 0–10, with a compound having formula VI, (VI) X(CO)R$^2$ in which X is hydroxyl or a carboxyl-activating leaving group and R$^2$ is selected from the group consisting of an amino acid or oligopeptide radical of up to 6 amino acids, a lipophilic radical formed from aliphatic or cycloaliphatic units, a combination of aliphatic and heterocyclic units, and a triphenylmethane dye, the branched tetrasaccharide Z of the compounds III, IV, or V being employed in protected or unprotected form.

20. The process as claimed in claim 19, wherein X in compound IV is an O-succinimidyl group.

21. The process as claimed in claim 19, wherein pyridine is employed as a solvent.

22. The process as claimed in claim 19, wherein N,N-dimethylformamide is employed as a solvent.

23. A pharmaceutical composition containing the compound as claimed in claim 1 and a pharmaceutically acceptable excipient, additive, solvent, or auxiliary.

24. A process for the preparation of a compound according to claim 1, comprising reacting a compound selected from the group consisting of a compound having formula III, (III) Z—O—(CH$_2$)$_n$—NH$_2$ a compound having formula IV, (IV) Z—NH$_2$ and a compound having formula V, (V) Z—NH(CO)—(CH$_2$)$_n$—NH$_2$ wherein Z is selected from the group consisting of sialyl Lewis A and sialyl Lewis X, with a compound having formula VI, (VI) X(CO)R$^2$ wherein X is hydroxyl or a carboxyl activating leaving group and R$^2$ is selected from the group consisting of an amino acid or oligopeptide radical of up to 6 amino acids, a lipophilic radical formed from aliphatic or cycloaliphatic units, a combination of aliphatic and heterocyclic units, and a triphenylmethane dye.

25. The process according to claim 24, wherein Z is in protected form.

26. The process according to claim 24, wherein Z is in unprotected form.

27. A process for the preparation of a compound according to claim 1, comprising the step of reacting a compound selected from the group consisting of a compound having formula III, (III) Z—O—(CH$_2$)$_n$—NH$_2$ a compound having formula IV, (IV) Z—NH$_2$ and a compound having formula V, (V) Z—NH(CO)—(CH$_2$)$_n$—NH$_2$ wherein Z is a branched tetrasaccharide and n is 0–10, with a compound of formula VI, (VI) X(CO)R$^2$ wherein X is hydroxyl or a carboxyl activating leaving group and R$^2$ is $$\begin{array}{l} -(CH_2)_m-[NH(CO)]_q-CH_2-CH_2 \\ X(CO)-(CH_2)_m-[NH(CO)]_q-CH_2-CH_2-C-NO_2 \\ X(CO)-(CH_2)_m-[NH(CO)]_q-CH_2-CH_2 \end{array}$$

wherein m is 0–10, p is 0 or 1, and q is 0 or 1, provided that when m=0, either p or q is equal to 0.

28. A method of preparing a pharmaceutical composition, comprising admixing the compound according to claim 1 with a pharmaceutically acceptable excipient, additive, solvent, or auxiliary.

29. The compound according to claim 1, wherein p is 1.

30. The compound according to claim 1, wherein Y is oxygen.

31. The compound according to claim 1, wherein R$^2$ is an oligopeptide radical containing up to 6 amino acids.

32. The compound according to claim 31, wherein Z comprises a carboxylic acid group.

33. The compound according to claim 32, wherein Z comprises a sialic acid residue.

34. The compound according to claim 1, wherein n is 0, 6, or 10.

* * * * *